US007041284B2

(12) United States Patent
Gregory et al.

(10) Patent No.: US 7,041,284 B2
(45) Date of Patent: May 9, 2006

(54) RECOMBINANT ADENOVIRAL VECTOR AND METHOD OF USE

(75) Inventors: Richard J. Gregory, Carlsbad, CA (US); Ken N. Wills, Encinitas, CA (US); Daniel C. Maneval, San Diego, CA (US)

(73) Assignee: Canji, Inc., San Diego, CA (US)

( * ) Notice: Subject to any disclaimer, the term of this patent is extended or adjusted under 35 U.S.C. 154(b) by 0 days.

(21) Appl. No.: 08/958,570

(22) Filed: Oct. 28, 1997

(65) Prior Publication Data

US 2001/0016192 A1 Aug. 23, 2001

Related U.S. Application Data

(63) Continuation of application No. 08/328,673, filed on Oct. 25, 1994, now Pat. No. 6,210,939, which is a continuation-in-part of application No. 08/246,006, filed on May 19, 1994, now abandoned, which is a continuation-in-part of application No. 08/142,669, filed on Oct. 25, 1993, now abandoned.

(51) Int. Cl.

| | |
|---|---|
| *A61K 48/00* | (2006.01) |
| *C12N 15/861* | (2006.01) |
| *C12N 15/63* | (2006.01) |

(52) U.S. Cl. .................... 424/93.2; 424/93.1; 424/93.6; 435/320.1; 435/69.1; 435/455; 435/456; 435/325

(58) Field of Classification Search ................ 424/93.1, 424/93.2, 93.6; 435/320.1, 69.1, 455, 456, 435/457, 325, 172.1, 172.3; 455/455, 456, 455/457, 69.1, 320.1, 325
See application file for complete search history.

(56) References Cited

U.S. PATENT DOCUMENTS 6,290,949 B1 9/2001 French et al.
6,333,030 B1 12/2001 Curiel
6,503,501 B1 1/2003 Anderson et al.
6,613,563 B1 9/2003 Sosnowski et al.
2003/0091534 A1 * 5/2003 Gregory et al. ............ 424/93.2

OTHER PUBLICATIONS

Buller et al., Cancer Gene Therapy, vol. 9, 2002, pp. 553–566.*
Kuball et al., Journal of Clinical Oncology, vol. 20, No. 4, 2002, pp. 957–965.*
Marshall, Science, vol. 299, 2003, p. 320.*
Fox, Nature Biotechnology, vol. 18, 2000, pp. 143–144.*
Gomez–Navarro et al., European Journal of Cancer, vol. 35, No. 6, 1999, pp. 867–885.*
Wen et al., Cancer Gene Therapy, vol. 10, 2003, pp. 224–238.*
W. French Anderson, Nature, vol. 392, pp. 25–30, Apr. 30, 1998.*
Gura, Science, vol. 278, pp. 1041–1042, Nov. 7, 1997.*
Twersky, "Girl's Parents Plead for Gene Therapy to Resume," WebMD Health, Sep. 27, 2000.
Weiss et al., "Methods Faulted in Fatal Gene Therapy," Washington Post, Dec. 8, 1999, p. A1.
"Gene Therapy Shows Promise for Fighting Cancer," ACS News Center, Aug. 21, 2000.

* cited by examiner

*Primary Examiner*—David Guzo
(74) *Attorney, Agent, or Firm*—Townsend and Townsend and Crew LLP

(57) ABSTRACT

This invention provides a recombinant adenovirus expression vector characterized by the partial or total deletion of the adenoviral protein IX DNA and having a gene encoding a foreign protein or a functional fragment or mutant thereof. Transformed host cells and a method of producing recombinant proteins and gene therapy also are included within the scope of this invention. Thus, for example, the adenoviral vector of this invention can contain a foreign gene for the expression of a protein effective in regulating the cell cycle, such as p53, Rb, or mitosin, or in inducing cell death, such as the conditional suicide gene thymidine dinase. (The latter must be used in conjunction with a thymidine kinase metabolite in order to be effective.)

32 Claims, 23 Drawing Sheets

```
Met Pro Pro Lys Thr Pro Arg Lys Thr Ala Ala Thr Ala Ala Ala Ala
 1               5                  10                   15

Ala Ala Glu Pro Pro Ala Pro Pro Pro Pro Pro Pro Pro Glu Glu Asp
            20                  25                  30

Pro Glu Gln Asp Ser Gly Pro Glu Asp Leu Pro Leu Val Arg Leu Glu
        35                  40                  45

Phe Glu Glu Thr Glu Glu Pro Asp Phe Thr Ala Leu Cys Gln Lys Leu
    50                  55                  60

Lys Ile Pro Asp His Val Arg Glu Arg Ala Trp Leu Thr Trp Glu Lys
65                  70                  75                  80

Val Ser Ser Val Asp Gly Val Leu Gly Gly Tyr Ile Gln Lys Lys Lys
                85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255
```

FIG. 2A

Gln Asn Arg Ser Ala Arg Ile Ala Lys Gln Leu Glu Asn Asp Thr Arg
260 265 270

Ile Ile Glu Val Leu Cys Lys Glu His Glu Cys Asn Ile Asp Glu Val
275 280 285

Lys Asn Val Tyr Phe Lys Asn Phe Ile Pro Phe Met Asn Ser Leu Gly
290 295 300

Leu Val Thr Ser Asn Gly Leu Pro Glu Val Glu Asn Leu Ser Lys Arg
305 310 315 320

Tyr Glu Glu Ile Tyr Leu Lys Asn Lys Asp Leu Asp Ala Arg Leu Phe
325 330 335

Leu Asp His Asp Lys Thr Leu Gln Thr Asp Ser Ile Asp Ser Phe Glu
340 345 350

Thr Gln Arg Thr Pro Arg Lys Ser Asn Leu Asp Glu Glu Val Asn Val
355 360 365

Ile Pro Pro His Thr Pro Val Arg Thr Val Met Asn Thr Ile Gln Gln
370 375 380

Leu Met Met Ile Leu Asn Ser Ala Ser Asp Gln Pro Ser Glu Asn Leu
385 390 395 400

Ile Ser Tyr Phe Asn Asn Cys Thr Val Asn Pro Lys Glu Ser Ile Leu
405 410 415

Lys Arg Val Lys Asp Ile Gly Tyr Ile Phe Lys Glu Lys Phe Ala Lys
420 425 430

Ala Val Gly Gln Gly Cys Val Glu Ile Gly Ser Gln Arg Tyr Lys Leu
435 440 445

Gly Val Arg Leu Tyr Tyr Arg Val Met Glu Ser Met Leu Lys Ser Glu
450 455 460

Glu Glu Arg Leu Ser Ile Gln Asn Phe Ser Lys Leu Leu Asn Asp Asn
465 470 475 480

Ile Phe His Met Ser Leu Leu Ala Cys Ala Leu Glu Val Val Met Ala
485 490 495

Thr Tyr Ser Arg Ser Thr Ser Gln Asn Leu Asp Ser Gly Thr Asp Leu
500 505 510

FIG. 2B

| | | | | | | | | | | | | | | | |
|---|---|---|---|---|---|---|---|---|---|---|---|---|---|---|---|
| Ser | Phe | Pro | Trp | Ile | Leu | Asn | Val | Leu | Asn | Leu | Lys | Ala | Phe | Asp | Phe |
| | | 515 | | | | | 520 | | | | | 525 | | | |
| Tyr | Lys | Val | Ile | Glu | Ser | Phe | Ile | Lys | Ala | Glu | Gly | Asn | Leu | Thr | Arg |
| | 530 | | | | | 535 | | | | | 540 | | | | |
| Glu | Met | Ile | Lys | His | Leu | Glu | Arg | Cys | Glu | His | Arg | Ile | Met | Glu | Ser |
| 545 | | | | | 550 | | | | | 555 | | | | | 560 |
| Leu | Ala | Trp | Leu | Ser | Asp | Ser | Pro | Leu | Phe | Asp | Leu | Ile | Lys | Gln | Ser |
| | | | | 565 | | | | | 570 | | | | | 575 | |
| Lys | Asp | Arg | Glu | Gly | Pro | Thr | Asp | His | Leu | Glu | Ser | Ala | Cys | Pro | Leu |
| | | | 580 | | | | | 585 | | | | | 590 | | |
| Asn | Leu | Pro | Leu | Gln | Asn | Asn | His | Thr | Ala | Ala | Asp | Met | Tyr | Leu | Ser |
| | | 595 | | | | | 600 | | | | | 605 | | | |
| Pro | Val | Arg | Ser | Pro | Lys | Lys | Lys | Gly | Ser | Thr | Thr | Arg | Val | Asn | Ser |
| | 610 | | | | | 615 | | | | | 620 | | | | |
| Thr | Ala | Asn | Ala | Glu | Thr | Gln | Ala | Thr | Ser | Ala | Phe | Gln | Thr | Gln | Lys |
| 625 | | | | | 630 | | | | | 635 | | | | | 640 |
| Pro | Leu | Lys | Ser | Thr | Ser | Leu | Ser | Leu | Phe | Tyr | Lys | Lys | Val | Tyr | Arg |
| | | | | 645 | | | | | 650 | | | | | 655 | |
| Leu | Ala | Tyr | Leu | Arg | Leu | Asn | Thr | Leu | Cys | Glu | Arg | Leu | Leu | Ser | Glu |
| | | | 660 | | | | | 665 | | | | | 670 | | |
| His | Pro | Glu | Leu | Glu | His | Ile | Ile | Trp | Thr | Leu | Phe | Gln | His | Thr | Leu |
| | | 675 | | | | | 680 | | | | | 685 | | | |
| Gln | Asn | Glu | Tyr | Glu | Leu | Met | Arg | Asp | Arg | His | Leu | Asp | Gln | Ile | Met |
| | 690 | | | | | 695 | | | | | 700 | | | | |
| Met | Cys | Ser | Met | Tyr | Gly | Ile | Cys | Lys | Val | Lys | Asn | Ile | Asp | Leu | Lys |
| 705 | | | | | 710 | | | | | 715 | | | | | 720 |
| Phe | Lys | Ile | Ile | Val | Thr | Ala | Tyr | Lys | Asp | Leu | Pro | His | Ala | Val | Gln |
| | | | | 725 | | | | | 730 | | | | | 735 | |
| Glu | Thr | Phe | Lys | Arg | Val | Leu | Ile | Lys | Glu | Glu | Glu | Tyr | Asp | Ser | Ile |
| | | | 740 | | | | | 745 | | | | | 750 | | |
| Ile | Val | Phe | Tyr | Asn | Ser | Val | Phe | Met | Gln | Arg | Leu | Lys | Thr | Asn | Ile |
| | | 755 | | | | | 760 | | | | | 765 | | | |

FIG. 2C

```
Leu Gln Tyr Ala Ser Thr Arg Pro Pro Thr Leu Ser Pro Ile Pro His
    770                 775                 780

Ile Pro Arg Ser Pro Tyr Lys Phe Pro Ser Ser Pro Leu Arg Ile Pro
785                 790                 795                 800

Gly Gly Asn Ile Tyr Ile Ser Pro Leu Lys Ser Pro Tyr Lys Ile Ser
                805                 810                 815

Glu Gly Leu Pro Thr Pro Thr Lys Met Thr Pro Arg Ser Arg Ile Leu
            820                 825                 830

Val Ser Ile Gly Glu Ser Phe Gly Thr Ser Glu Lys Phe Gln Lys Ile
        835                 840                 845

Asn Gln Met Val Cys Asn Ser Asp Arg Val Leu Lys Arg Ser Ala Glu
    850                 855                 860

Gly Ser Asn Pro Pro Lys Pro Leu Lys Lys Leu Arg Phe Asp Ile Glu
865                 870                 875                 880

Gly Ser Asp Glu Ala Asp Gly Ser Lys His Leu Pro Gly Glu Ser Lys
                885                 890                 895

Phe Gln Gln Lys Leu Ala Glu Met Thr Ser Thr Arg Thr Arg Met Gln
            900                 905                 910

Lys Gln Lys Met Asn Asp Ser Met Asp Thr Ser Asn Lys Glu Glu Lys
        915                 920                 925
```

FIG. 2D

```
TTCCGGTTTT TCTCAGGGGA CGTTGAAATT ATTTTTGTAA CGGGAGTCGG GAGAGGACGG    60

GGCGTGCCCC GCGTGCGCGC GCGTCGTCCT CCCCGGCGCT CCTCCACAGC TCGCTGGCTC   120

CCGCCGCGGA AAGGCGTC ATG CCG CCC AAA ACC CCC CGA AAA ACG GCC GCC     171
                    Met Pro Pro Lys Thr Pro Arg Lys Thr Ala Ala
                     1               5                  10

ACC GCC GCC GCT GCC GCC GCG GAA CCC CCG GCA CCG CCG CCG CCG CCC     219
Thr Ala Ala Ala Ala Ala Ala Glu Pro Pro Ala Pro Pro Pro Pro Pro
            15                  20                  25

CCT CCT GAG GAG GAC CCA GAG CAG GAC AGC GGC CCG GAG GAC CTG CCT     267
Pro Pro Glu Glu Asp Pro Glu Gln Asp Ser Gly Pro Glu Asp Leu Pro
        30                  35                  40

CTC GTC AGG CTT GAG TTT GAA GAA ACA GAA GAA CCT GAT TTT ACT GCA     315
Leu Val Arg Leu Glu Phe Glu Glu Thr Glu Glu Pro Asp Phe Thr Ala
    45                  50                  55

TTA TGT CAG AAA TTA AAG ATA CCA GAT CAT GTC AGA GAG AGA GCT TGG     363
Leu Cys Gln Lys Leu Lys Ile Pro Asp His Val Arg Glu Arg Ala Trp
60                  65                  70                  75

TTA ACT TGG GAG AAA GTT TCA TCT GTG GAT GGA GTA TTG GGA GGT TAT     411
Leu Thr Trp Glu Lys Val Ser Ser Val Asp Gly Val Leu Gly Gly Tyr
                80                  85                  90

ATT CAA AAG AAA AAG GAA CTG TGG GGA ATC TGT ATC TTT ATT GCA GCA     459
Ile Gln Lys Lys Lys Glu Leu Trp Gly Ile Cys Ile Phe Ile Ala Ala
            95                  100                 105

GTT GAC CTA GAT GAG ATG TCG TTC ACT TTT ACT GAG CTA CAG AAA AAC     507
Val Asp Leu Asp Glu Met Ser Phe Thr Phe Thr Glu Leu Gln Lys Asn
        110                 115                 120

ATA GAA ATC AGT GTC CAT AAA TTC TTT AAC TTA CTA AAA GAA ATT GAT     555
Ile Glu Ile Ser Val His Lys Phe Phe Asn Leu Leu Lys Glu Ile Asp
    125                 130                 135

ACC AGT ACC AAA GTT GAT AAT GCT ATG TCA AGA CTG TTG AAG AAG TAT     603
Thr Ser Thr Lys Val Asp Asn Ala Met Ser Arg Leu Leu Lys Lys Tyr
140                 145                 150                 155

GAT GTA TTG TTT GCA CTC TTC AGC AAA TTG GAA AGG ACA TGT GAA CTT     651
Asp Val Leu Phe Ala Leu Phe Ser Lys Leu Glu Arg Thr Cys Glu Leu
                160                 165                 170

ATA TAT TTG ACA CAA CCC AGC AGT TCG ATA TCT ACT GAA ATA AAT TCT     699
Ile Tyr Leu Thr Gln Pro Ser Ser Ser Ile Ser Thr Glu Ile Asn Ser
            175                 180                 185

GCA TTG GTG CTA AAA GTT TCT TGG ATC ACA TTT TTA TTA GCT AAA GGG     747
Ala Leu Val Leu Lys Val Ser Trp Ile Thr Phe Leu Leu Ala Lys Gly
        190                 195                 200

GAA GTA TTA CAA ATG GAA GAT GAT CTG GTG ATT TCA TTT CAG TTA ATG     795
Glu Val Leu Gln Met Glu Asp Asp Leu Val Ile Ser Phe Gln Leu Met
    205                 210                 215
```

FIG. 3A

CTA TGT GTC CTT GAC TAT TTT ATT AAA CTC TCA CCT CCC ATG TTG CTC 843
Leu Cys Val Leu Asp Tyr Phe Ile Lys Leu Ser Pro Pro Met Leu Leu
220 225 230 235

AAA GAA CCA TAT AAA ACA GCT GTT ATA CCC ATT AAT GGT TCA CCT CGA 891
Lys Glu Pro Tyr Lys Thr Ala Val Ile Pro Ile Asn Gly Ser Pro Arg
240 245 250

ACA CCC AGG CGA GGT CAG AAC AGG AGT GCA CGG ATA GCA AAA CAA CTA 939
Thr Pro Arg Arg Gly Gln Asn Arg Ser Ala Arg Ile Ala Lys Gln Leu
255 260 265

GAA AAT GAT ACA AGA ATT ATT GAA GTT CTC TGT AAA GAA CAT GAA TGT 987
Glu Asn Asp Thr Arg Ile Ile Glu Val Leu Cys Lys Glu His Glu Cys
270 275 280

AAT ATA GAT GAG GTG AAA AAT GTT TAT TTC AAA AAT TTT ATA CCT TTT 1035
Asn Ile Asp Glu Val Lys Asn Val Tyr Phe Lys Asn Phe Ile Pro Phe
285 290 295

ATG AAT TCT CTT GGA CTT GTA ACA TCT AAT GGA CTT CCA GAG GTT GAA 1083
Met Asn Ser Leu Gly Leu Val Thr Ser Asn Gly Leu Pro Glu Val Glu
300 305 310 315

AAT CTT TCT AAA CGA TAC GAA GAA ATT TAT CTT AAA AAT AAA GAT CTA 1131
Asn Leu Ser Lys Arg Tyr Glu Glu Ile Tyr Leu Lys Asn Lys Asp Leu
320 325 330

GAT GCA AGA TTA TTT TTG GAT CAT GAT AAA ACT CTT CAG ACT GAT TCT 1179
Asp Ala Arg Leu Phe Leu Asp His Asp Lys Thr Leu Gln Thr Asp Ser
335 340 345

ATA GAC AGT TTT GAA ACA CAG AGA ACA CCA CGA AAA AGT AAC CTT GAT 1227
Ile Asp Ser Phe Glu Thr Gln Arg Thr Pro Arg Lys Ser Asn Leu Asp
350 355 360

GAA GAG GTG AAT GTA ATT CCT CCA CAC ACT CCA GTT AGG ACT GTT ATG 1275
Glu Glu Val Asn Val Ile Pro Pro His Thr Pro Val Arg Thr Val Met
365 370 375

AAC ACT ATC CAA CAA TTA ATG ATG ATT TTA AAT TCA GCA AGT GAT CAA 1323
Asn Thr Ile Gln Gln Leu Met Met Ile Leu Asn Ser Ala Ser Asp Gln
380 385 390 395

CCT TCA GAA AAT CTG ATT TCC TAT TTT AAC AAC TGC ACA GTG AAT CCA 1371
Pro Ser Glu Asn Leu Ile Ser Tyr Phe Asn Asn Cys Thr Val Asn Pro
400 405 410

AAA GAA AGT ATA CTG AAA AGA GTG AAG GAT ATA GGA TAC ATC TTT AAA 1419
Lys Glu Ser Ile Leu Lys Arg Val Lys Asp Ile Gly Tyr Ile Phe Lys
415 420 425

GAG AAA TTT GCT AAA GCT GTG GGA CAG GGT TGT GTC GAA ATT GGA TCA 1467
Glu Lys Phe Ala Lys Ala Val Gly Gln Gly Cys Val Glu Ile Gly Ser
430 435 440

CAG CGA TAC AAA CTT GGA GTT CGC TTG TAT TAC CGA GTA ATG GAA TCC 1515
Gln Arg Tyr Lys Leu Gly Val Arg Leu Tyr Tyr Arg Val Met Glu Ser
445 450 455

FIG. 3B

ATG CTT AAA TCA GAA GAA GAA CGA TTA TCC ATT CAA AAT TTT AGC AAA 1563
Met Leu Lys Ser Glu Glu Glu Arg Leu Ser Ile Gln Asn Phe Ser Lys
460 465 470 475

CTT CTG AAT GAC AAC ATT TTT CAT ATG TCT TTA TTG GCG TGC GCT CTT 1611
Leu Leu Asn Asp Asn Ile Phe His Met Ser Leu Leu Ala Cys Ala Leu
480 485 490

GAG GTT GTA ATG GCC ACA TAT AGC AGA AGT ACA TCT CAG AAT CTT GAT 1659
Glu Val Val Met Ala Thr Tyr Ser Arg Ser Thr Ser Gln Asn Leu Asp
495 500 505

TCT GGA ACA GAT TTG TCT TTC CCA TGG ATT CTG AAT GTG CTT AAT TTA 1707
Ser Gly Thr Asp Leu Ser Phe Pro Trp Ile Leu Asn Val Leu Asn Leu
510 515 520

AAA GCC TTT GAT TTT TAC AAA GTG ATC GAA AGT TTT ATC AAA GCA GAA 1755
Lys Ala Phe Asp Phe Tyr Lys Val Ile Glu Ser Phe Ile Lys Ala Glu
525 530 535

GGC AAC TTG ACA AGA GAA ATG ATA AAA CAT TTA GAA CGA TGT GAA CAT 1803
Gly Asn Leu Thr Arg Glu Met Ile Lys His Leu Glu Arg Cys Glu His
540 545 550 555

CGA ATC ATG GAA TCC CTT GCA TGG CTC TCA GAT TCA CCT TTA TTT GAT 1851
Arg Ile Met Glu Ser Leu Ala Trp Leu Ser Asp Ser Pro Leu Phe Asp
560 565 570

CTT ATT AAA CAA TCA AAG GAC CGA GAA GGA CCA ACT GAT CAC CTT GAA 1899
Leu Ile Lys Gln Ser Lys Asp Arg Glu Gly Pro Thr Asp His Leu Glu
575 580 585

TCT GCT TGT CCT CTT AAT CTT CCT CTC CAG AAT AAT CAC ACT GCA GCA 1947
Ser Ala Cys Pro Leu Asn Leu Pro Leu Gln Asn Asn His Thr Ala Ala
590 595 600

GAT ATG TAT CTT TCT CCT GTA AGA TCT CCA AAG AAA AAA GGT TCA ACT 1995
Asp Met Tyr Leu Ser Pro Val Arg Ser Pro Lys Lys Lys Gly Ser Thr
605 610 615

ACG CGT GTA AAT TCT ACT GCA AAT GCA GAG ACA CAA GCA ACC TCA GCC 2043
Thr Arg Val Asn Ser Thr Ala Asn Ala Glu Thr Gln Ala Thr Ser Ala
620 625 630 635

TTC CAG ACC CAG AAG CCA TTG AAA TCT ACC TCT CTT TCA CTG TTT TAT 2091
Phe Gln Thr Gln Lys Pro Leu Lys Ser Thr Ser Leu Ser Leu Phe Tyr
640 645 650

AAA AAA GTG TAT CGG CTA GCC TAT CTC CGG CTA AAT ACA CTT TGT GAA 2139
Lys Lys Val Tyr Arg Leu Ala Tyr Leu Arg Leu Asn Thr Leu Cys Glu
655 660 665

CGC CTT CTG TCT GAG CAC CCA GAA TTA GAA CAT ATC ATC TGG ACC CTT 2187
Arg Leu Leu Ser Glu His Pro Glu Leu Glu His Ile Ile Trp Thr Leu
670 675 680

TTC CAG CAC ACC CTG CAG AAT GAG TAT GAA CTC ATG AGA GAC AGG CAT 2235
Phe Gln His Thr Leu Gln Asn Glu Tyr Glu Leu Met Arg Asp Arg His
685 690 695

FIG. 3C

```
TTG GAC CAA ATT ATG ATG TGT TCC ATG TAT GGC ATA TGC AAA GTG AAG  2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT  2331
Asn Ile Asp Leu Lys Phe Lys Ile Ile Val Thr Ala Tyr Lys Asp Leu
                720                 725                 730

CCT CAT GCT GTT CAG GAG ACA TTC AAA CGT GTT TTG ATC AAA GAA GAG  2379
Pro His Ala Val Gln Glu Thr Phe Lys Arg Val Leu Ile Lys Glu Glu
            735                 740                 745

GAG TAT GAT TCT ATT ATA GTA TTC TAT AAC TCG GTC TTC ATG CAG AGA  2427
Glu Tyr Asp Ser Ile Ile Val Phe Tyr Asn Ser Val Phe Met Gln Arg
        750                 755                 760

CTG AAA ACA AAT ATT TTG CAG TAT GCT TCC ACC AGG CCC CCT ACC TTG  2475
Leu Lys Thr Asn Ile Leu Gln Tyr Ala Ser Thr Arg Pro Pro Thr Leu
    765                 770                 775

TCA CCA ATA CCT CAC ATT CCT CGA AGC CCT TAC AAG TTT CCT AGT TCA  2523
Ser Pro Ile Pro His Ile Pro Arg Ser Pro Tyr Lys Phe Pro Ser Ser
780                 785                 790                 795

CCC TTA CGG ATT CCT GGA GGG AAC ATC TAT ATT TCA CCC CTG AAG AGT  2571
Pro Leu Arg Ile Pro Gly Gly Asn Ile Tyr Ile Ser Pro Leu Lys Ser
                800                 805                 810

CCA TAT AAA ATT TCA GAA GGT CTG CCA ACA CCA ACA AAA ATG ACT CCA  2619
Pro Tyr Lys Ile Ser Glu Gly Leu Pro Thr Pro Thr Lys Met Thr Pro
            815                 820                 825

AGA TCA AGA ATC TTA GTA TCA ATT GGT GAA TCA TTC GGG ACT TCT GAG  2667
Arg Ser Arg Ile Leu Val Ser Ile Gly Glu Ser Phe Gly Thr Ser Glu
        830                 835                 840

AAG TTC CAG AAA ATA AAT CAG ATG GTA TGT AAC AGC GAC CGT GTG CTC  2715
Lys Phe Gln Lys Ile Asn Gln Met Val Cys Asn Ser Asp Arg Val Leu
    845                 850                 855

AAA AGA AGT GCT GAA GGA AGC AAC CCT CCT AAA CCA CTG AAA AAA CTA  2763
Lys Arg Ser Ala Glu Gly Ser Asn Pro Pro Lys Pro Leu Lys Lys Leu
860                 865                 870                 875

CGC TTT GAT ATT GAA GGA TCA GAT GAA GCA GAT GGA AGT AAA CAT CTC  2811
Arg Phe Asp Ile Glu Gly Ser Asp Glu Ala Asp Gly Ser Lys His Leu
                880                 885                 890

CCA GGA GAG TCC AAA TTT CAG CAG AAA CTG GCA GAA ATG ACT TCT ACT  2859
Pro Gly Glu Ser Lys Phe Gln Gln Lys Leu Ala Glu Met Thr Ser Thr
            895                 900                 905

CGA ACA CGA ATG CAA AAG CAG AAA ATG AAT GAT AGC ATG GAT ACC TCA  2907
Arg Thr Arg Met Gln Lys Gln Lys Met Asn Asp Ser Met Asp Thr Ser
        910                 915                 920

AAC AAG GAA GAG AAA TGAGGATCTC AGGACCTTGG TGGACACTGT GTACACCTCT  2962
Asn Lys Glu Glu Lys
    925

GGATTCATTG TCTCTCACAG ATGTGACTGA TAT                             2995
```

FIG. 3D

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 1:

CGCCACCGAG GGACCTGAGC GAGTC 25

(2) INFORMATION FOR SEQ ID NO: 2:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 2:

TTCTGGGAAG GGACAGAAGA 20

(2) INFORMATION FOR SEQ ID NO: 3:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 3:

CGCGCTAGCT CTGCCCCAAA GAGCT 25

(2) INFORMATION FOR SEQ ID NO: 4:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 4:

CGCGGTACCC TCGAGTCTAG ATATTGCCAG TGGTGGAAG 39

(2) INFORMATION FOR SEQ ID NO: 5:

(i) SEQUENCE CHARACTERISTICS:
(A) LENGTH: 35 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO: 5:

-continued

```
CGTGCGGCCG CTGGAGGACT TTGAGGATGT CTGTC                          35


(2) INFORMATION FOR SEQ ID NO: 6:

     (i) SEQUENCE CHARACTERISTICS:
          (A) LENGTH: 33 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO: 6:

CGCTCTAGAG AGACCAGTTA GGAAGTTTTC GCA                            33


(2) INFORMATION FOR SEQ ID NO: 7:

     (i) SEQUENCE CHARACTERISTICS:
          (A) LENGTH: 2995 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 139..2925
          (D) OTHER INFORMATION: /product= "RB"
               /note= "retinoblastoma tumor suppressor"

    (xi) SEQUENCE DESCRIPTION: SEQ ID NO: 7:

TTCCGGTTTT TCTCAGGGGA CGTTGAAATT ATTTTTGTAA CGGGAGTCGG GAGAGGACGG     60

GGCGTGCCCC GCGTGCGCGC GCGTCGTCCT CCCCGGCGCT CCTCCACAGC TCGCTGGCT     120

CCGCCGCGGA AAGGCGTC ATG CCG CCC AAA ACC CCC CGA AAA ACG GCC GCC      171
                    Met Pro Pro Lys Thr Pro Arg Lys Thr Ala Ala
                      1               5                  10

ACC GCC GCC GCT GCC GCC GCG GAA CCC CCG GCA CCG CCG CCG CCG CCC      219
Thr Ala Ala Ala Ala Ala Ala Glu Pro Pro Ala Pro Pro Pro Pro Pro
            15                  20                  25

CCT CCT GAG GAG GAC CCA GAG CAG GAC AGC GGC CCG GAG GAC CTG CCT      267
Pro Pro Glu Glu Asp Pro Glu Gln Asp Ser Gly Pro Glu Asp Leu Pro
        30                  35                  40

CTC GTC AGG CTT GAG TTT GAA GAA ACA GAA GAA CCT GAT TTT ACT GCA      315
Leu Val Arg Leu Glu Phe Glu Glu Thr Glu Glu Pro Asp Phe Thr Ala
    45                  50                  55

TTA TGT CAG AAA TTA AAG ATA CCA GAT CAT GTC AGA GAG AGA GCT TGG      363
Leu Cys Gln Lys Leu Lys Ile Pro Asp His Val Arg Glu Arg Ala Trp
 60                  65                  70                  75

TTA ACT TGG GAG AAA GTT TCA TCT GTG GAT GGA GTA TTG GGA GGT TAT      411
Leu Thr Trp Glu Lys Val Ser Ser Val Asp Gly Val Leu Gly Gly Tyr
                80                  85                  90

ATT CAA AAG AAA AAG GAA CTG TGG GGA ATC TGT ATC TTT ATT GCA GCA      459
Ile Gln Lys Lys Lys Glu Leu Trp Gly Ile Cys Ile Phe Ile Ala Ala
            95                 100                 105

GTT GAC CTA GAT GAG ATG TCG TTC ACT TTT ACT GAG CTA CAG AAA AAC      507
Val Asp Leu Asp Glu Met Ser Phe Thr Phe Thr Glu Leu Gln Lys Asn
        110                 115                 120

ATA GAA ATC AGT GTC CAT AAA TTC TTT AAC TTA CTA AAA GAA ATT GAT      555
Ile Glu Ile Ser Val His Lys Phe Phe Asn Leu Leu Lys Glu Ile Asp
    125                 130                 135

ACC AGT ACC AAA GTT GAT AAT GCT ATG TCA AGA CTG TTG AAG AAG TAT      603
Thr Ser Thr Lys Val Asp Asn Ala Met Ser Arg Leu Leu Lys Lys Tyr
```

-continued

```
140                 145                 150                 155

GAT GTA TTG TTT GCA CTC TTC AGC AAA TTG GAA AGG ACA TGT GAA CTT      651
Asp Val Leu Phe Ala Leu Phe Ser Lys Leu Glu Arg Thr Cys Glu Leu
                160                 165                 170

ATA TAT TTG ACA CAA CCC AGC AGT TCG ATA TCT ACT GAA ATA AAT TCT      699
Ile Tyr Leu Thr Gln Pro Ser Ser Ser Ile Ser Thr Glu Ile Asn Ser
            175                 180                 185

GCA TTG GTG CTA AAA GTT TCT TGG ATC ACA TTT TTA TTA GCT AAA GGG      747
Ala Leu Val Leu Lys Val Ser Trp Ile Thr Phe Leu Leu Ala Lys Gly
        190                 195                 200

GAA GTA TTA CAA ATG GAA GAT GAT CTG GTG ATT TCA TTT CAG TTA ATG      795
Glu Val Leu Gln Met Glu Asp Asp Leu Val Ile Ser Phe Gln Leu Met
    205                 210                 215

CTA TGT GTC CTT GAC TAT TTT ATT AAA CTC TCA CCT CCC ATG TTG CTC      843
Leu Cys Val Leu Asp Tyr Phe Ile Lys Leu Ser Pro Pro Met Leu Leu
220                 225                 230                 235

AAA GAA CCA TAT AAA ACA GCT GTT ATA CCC ATT AAT GGT TCA CCT CGA      891
Lys Glu Pro Tyr Lys Thr Ala Val Ile Pro Ile Asn Gly Ser Pro Arg
                240                 245                 250

ACA CCC AGG CGA GGT CAG AAC AGG AGT GCA CGG ATA GCA AAA CAA CTA      939
Thr Pro Arg Arg Gly Gln Asn Arg Ser Ala Arg Ile Ala Lys Gln Leu
            255                 260                 265

GAA AAT GAT ACA AGA ATT ATT GAA GTT CTC TGT AAA GAA CAT GAA TGT      987
Glu Asn Asp Thr Arg Ile Ile Glu Val Leu Cys Lys Glu His Glu Cys
        270                 275                 280

AAT ATA GAT GAG GTG AAA AAT GTT TAT TTC AAA AAT TTT ATA CCT TTT1     035
Asn Ile Asp Glu Val Lys Asn Val Tyr Phe Lys Asn Phe Ile Pro Phe
    285                 290                 295

ATG AAT TCT CTT GGA CTT GTA ACA TCT AAT GGA CTT CCA GAG GTT GAA1     083
Met Asn Ser Leu Gly Leu Val Thr Ser Asn Gly Leu Pro Glu Val Glu
300                 305                 310                 315

AAT CTT TCT AAA CGA TAC GAA GAA ATT TAT CTT AAA AAT AAA GAT CTA     1131
Asn Leu Ser Lys Arg Tyr Glu Glu Ile Tyr Leu Lys Asn Lys Asp Leu
                320                 325                 330

GAT GCA AGA TTA TTT TTG GAT CAT GAT AAA ACT CTT CAG ACT GAT TCT     1179
Asp Ala Arg Leu Phe Leu Asp His Asp Lys Thr Leu Gln Thr Asp Ser
            335                 340                 345

ATA GAC AGT TTT GAA ACA CAG AGA ACA CCA CGA AAA AGT AAC CTT GAT     1227
Ile Asp Ser Phe Glu Thr Gln Arg Thr Pro Arg Lys Ser Asn Leu Asp
        350                 355                 360

GAA GAG GTG AAT GTA ATT CTT CCA CAC ACT CCA GTT AGG ACT GTT ATG     1275
Glu Glu Val Asn Val Ile Leu Pro His Thr Pro Val Arg Thr Val Met
    365                 370                 375

AAC ACT ATC CAA CAA TTA ATG ATG ATT TTA AAT TCA GCA AGT GAT CAA     1323
Asn Thr Ile Gln Gln Leu Met Met Ile Leu Asn Ser Ala Ser Asp Gln
380                 385                 390                 395

CCT TCA GAA AAT CTG ATT TCC TAT TTT AAC AAC TGC ACA GTG AAT CCA     1371
Pro Ser Glu Asn Leu Ile Ser Tyr Phe Asn Asn Cys Thr Val Asn Pro
                400                 405                 410

AAA GAA AGT ATA CTG AAA AGA GTG AAG GAT ATA GGA TAC ATC TTT AAA     1419
Lys Glu Ser Ile Leu Lys Arg Val Lys Asp Ile Gly Tyr Ile Phe Lys
            415                 420                 425

GAG AAA TTT GCT AAA GCT GTG GGA CAG GGT TGT GTC GAA ATT GGA TCA     1467
Glu Lys Phe Ala Lys Ala Val Gly Gln Gly Cys Val Glu Ile Gly Ser
        430                 435                 440

CAG CGA TAC AAA CTT GGA GTT CGC TTG TAT TAC CGA GTA ATG GAA TCC     1515
Gln Arg Tyr Lys Leu Gly Val Arg Leu Tyr Tyr Arg Val Met Glu Ser
    445                 450                 455

ATG CTT AAA TCA GAA GAA GAA CGA TTA TCC ATT CAA AAT TTT AGC AAA     1563
```

-continued

```
Met Leu Lys Ser Glu Glu Glu Arg Leu Ser Ile Gln Asn Phe Ser Lys
460                 465                 470                 475

CTT CTG AAT GAC AAC ATT TTT CAT ATG TCT TTA TTG GCG TGC GCT CTT      1611
Leu Leu Asn Asp Asn Ile Phe His Met Ser Leu Leu Ala Cys Ala Leu
                480                 485                 490

GAG GTT GTA ATG GCC ACA TAT AGC AGA AGT ACA TCT CAG AAT CTT GAT      1659
Glu Val Val Met Ala Thr Tyr Ser Arg Ser Thr Ser Gln Asn Leu Asp
            495                 500                 505

TCT GGA ACA GAT TTG TCT TTC CCA TGG ATT CTG AAT GTG CTT AAT TTA      1707
Ser Gly Thr Asp Leu Ser Phe Pro Trp Ile Leu Asn Val Leu Asn Leu
        510                 515                 520

AAA GCC TTT GAT TTT TAC AAA GTG ATC GAA AGT TTT ATC AAA GCA GAA      1755
Lys Ala Phe Asp Phe Tyr Lys Val Ile Glu Ser Phe Ile Lys Ala Glu
    525                 530                 535

GGC AAC TTG ACA AGA GAA ATG ATA AAA CAT TTA GAA CGA TGT GAA CAT      1803
Gly Asn Leu Thr Arg Glu Met Ile Lys His Leu Glu Arg Cys Glu His
540                 545                 550                 555

CGA ATC ATG GAA TCC CTT GCA TGG CTC TCA GAT TCA CCT TTA TTT GAT      1851
Arg Ile Met Glu Ser Leu Ala Trp Leu Ser Asp Ser Pro Leu Phe Asp
                560                 565                 570

CTT ATT AAA CAA TCA AAG GAC CGA GAA GGA CCA ACT GAT CAC CTT GAA      1899
Leu Ile Lys Gln Ser Lys Asp Arg Glu Gly Pro Thr Asp His Leu Glu
            575                 580                 585

TCT GCT TGT CCT CTT AAT CTT CCT CTC CAG AAT AAT CAC ACT GCA GCA      1947
Ser Ala Cys Pro Leu Asn Leu Pro Leu Gln Asn Asn His Thr Ala Ala
        590                 595                 600

GAT ATG TAT CTT TCT CCT GTA AGA TCT CCA AAG AAA AAA GGT TCA ACT      1995
Asp Met Tyr Leu Ser Pro Val Arg Ser Pro Lys Lys Lys Gly Ser Thr
    605                 610                 615

ACG CGT GTA AAT TCT ACT GCA AAT GCA GAG ACA CAA GCA ACC TCA GCC      2043
Thr Arg Val Asn Ser Thr Ala Asn Ala Glu Thr Gln Ala Thr Ser Ala
620                 625                 630                 635

TTC CAG ACC CAG AAG CCA TTG AAA TCT ACC TCT CTT TCA CTG TTT TAT      2091
Phe Gln Thr Gln Lys Pro Leu Lys Ser Thr Ser Leu Ser Leu Phe Tyr
                640                 645                 650

AAA AAA GTG TAT CGG CTA GCC TAT CTC CGG CTA AAT ACA CTT TGT GAA      2139
Lys Lys Val Tyr Arg Leu Ala Tyr Leu Arg Leu Asn Thr Leu Cys Glu
            655                 660                 665

CGC CTT CTG TCT GAG CAC CCA GAA TTA GAA CAT ATC ATC TGG ACC CTT      2187
Arg Leu Leu Ser Glu His Pro Glu Leu Glu His Ile Ile Trp Thr Leu
        670                 675                 680

TTC CAG CAC ACC CTG CAG AAT GAG TAT GAA CTC ATG AGA GAC AGG CAT      2235
Phe Gln His Thr Leu Gln Asn Glu Tyr Glu Leu Met Arg Asp Arg His
    685                 690                 695

TTG GAC CAA ATT ATG ATG TGT TCC ATG TAT GGC ATA TGC AAA GTG AAG      2283
Leu Asp Gln Ile Met Met Cys Ser Met Tyr Gly Ile Cys Lys Val Lys
700                 705                 710                 715

AAT ATA GAC CTT AAA TTC AAA ATC ATT GTA ACA GCA TAC AAG GAT CTT      2331
Asn Ile Asp Leu Lys Phe Lys Ile Ile Val Thr Ala Tyr Lys Asp Leu
                720                 725                 730

CCT CAT GCT GTT CAG GAG ACA TTC AAA CGT GTT TTG ATC AAA GAA GAG      2379
Pro His Ala Val Gln Glu Thr Phe Lys Arg Val Leu Ile Lys Glu Glu
            735                 740                 745

GAG TAT GAT TCT ATT ATA GTA TTC TAT AAC TCG GTC TTC ATG CAG AGA      2427
Glu Tyr Asp Ser Ile Ile Val Phe Tyr Asn Ser Val Phe Met Gln Arg
        750                 755                 760

CTG AAA ACA AAT ATT TTG CAG TAT GCT TCC ACC AGG CCC CCT ACC TTG      2475
Leu Lys Thr Asn Ile Leu Gln Tyr Ala Ser Thr Arg Pro Pro Thr Leu
    765                 770                 775
```

-continued

```
TCA CCA ATA CCT CAC ATT CCT CGA AGC CCT TAC AAG TTT CCT AGT TCA      2523
Ser Pro Ile Pro His Ile Pro Arg Ser Pro Tyr Lys Phe Pro Ser Ser
780                 785                 790                 795

CCC TTA CGG ATT CCT GGA GGG AAC ATC TAT ATT TCA CCC CTG AAG AGT      2571
Pro Leu Arg Ile Pro Gly Gly Asn Ile Tyr Ile Ser Pro Leu Lys Ser
                800                 805                 810

CCA TAT AAA ATT TCA GAA GGT CTG CCA ACA CCA ACA AAA ATG ACT CCA      2619
Pro Tyr Lys Ile Ser Glu Gly Leu Pro Thr Pro Thr Lys Met Thr Pro
            815                 820                 825

AGA TCA AGA ATC TTA GTA TCA ATT GGT GAA TCA TTC GGG ACT TCT GAG      2667
Arg Ser Arg Ile Leu Val Ser Ile Gly Glu Ser Phe Gly Thr Ser Glu
        830                 835                 840

AAG TTC CAG AAA ATA AAT CAG ATG GTA TGT AAC AGC GAC CGT GTG CTC      2715
Lys Phe Gln Lys Ile Asn Gln Met Val Cys Asn Ser Asp Arg Val Leu
    845                 850                 855

AAA AGA AGT GCT GAA GGA AGC AAC CCT CCT AAA CCA CTG AAA AAA CTA      2763
Lys Arg Ser Ala Glu Gly Ser Asn Pro Pro Lys Pro Leu Lys Lys Leu
860                 865                 870                 875

CGC TTT GAT ATT GAA GGA TCA GAT GAA GCA GAT GGA AGT AAA CAT CTC      2811
Arg Phe Asp Ile Glu Gly Ser Asp Glu Ala Asp Gly Ser Lys His Leu
                880                 885                 890

CCA GGA GAG TCC AAA TTT CAG CAG AAA CTG GCA GAA ATG ACT TCT ACT      2859
Pro Gly Glu Ser Lys Phe Gln Gln Lys Leu Ala Glu Met Thr Ser Thr
            895                 900                 905

CGA ACA CGA ATG CAA AAG CAG AAA ATG AAT GAT AGC ATG GAT ACC TCA      2907
Arg Thr Arg Met Gln Lys Gln Lys Met Asn Asp Ser Met Asp Thr Ser
        910                 915                 920

AAC AAG GAA GAG AAA TGAGGATCTC AGGACCTTGG TGGACACTGT GTACACCTCT      2962
Asn Lys Glu Glu Lys
    925

GGATTCATTG TCTCTCACAG ATGTGACTGA TAT                                 2995
```

(2) INFORMATION FOR SEQ ID NO: 8:

(i) SEQUENCE CHARACTERISTICS:
(A) LENGTH: 928 amino acids
(B) TYPE: amino acid
(D) TOPOLOGY: linear (ii) MOLECULE TYPE: protein (xi) SEQUENCE DESCRIPTION: SEQ ID NO: 8:

```
Met Pro Pro Lys Thr Pro Arg Lys Thr Ala Ala Thr Ala Ala Ala Ala
  1               5                  10                  15

Ala Ala Glu Pro Pro Ala Pro Pro Pro Pro Pro Pro Pro Glu Glu Asp
             20                  25                  30

Pro Glu Gln Asp Ser Gly Pro Glu Asp Leu Pro Leu Val Arg Leu Glu
         35                  40                  45

Phe Glu Glu Thr Glu Glu Pro Asp Phe Thr Ala Leu Cys Gln Lys Leu
     50                  55                  60

Lys Ile Pro Asp His Val Arg Glu Arg Ala Trp Leu Thr Trp Glu Lys
 65                  70                  75                  80

Val Ser Ser Val Asp Gly Val Leu Gly Gly Tyr Ile Gln Lys Lys Lys
                 85                  90                  95

Glu Leu Trp Gly Ile Cys Ile Phe Ile Ala Ala Val Asp Leu Asp Glu
            100                 105                 110

Met Ser Phe Thr Phe Thr Glu Leu Gln Lys Asn Ile Glu Ile Ser Val
        115                 120                 125

His Lys Phe Phe Asn Leu Leu Lys Glu Ile Asp Thr Ser Thr Lys Val
```

-continued

```
    130                 135                 140

Asp Asn Ala Met Ser Arg Leu Leu Lys Lys Tyr Asp Val Leu Phe Ala
145                 150                 155                 160

Leu Phe Ser Lys Leu Glu Arg Thr Cys Glu Leu Ile Tyr Leu Thr Gln
                165                 170                 175

Pro Ser Ser Ser Ile Ser Thr Glu Ile Asn Ser Ala Leu Val Leu Lys
            180                 185                 190

Val Ser Trp Ile Thr Phe Leu Leu Ala Lys Gly Glu Val Leu Gln Met
        195                 200                 205

Glu Asp Asp Leu Val Ile Ser Phe Gln Leu Met Leu Cys Val Leu Asp
    210                 215                 220

Tyr Phe Ile Lys Leu Ser Pro Pro Met Leu Leu Lys Glu Pro Tyr Lys
225                 230                 235                 240

Thr Ala Val Ile Pro Ile Asn Gly Ser Pro Arg Thr Pro Arg Arg Gly
                245                 250                 255

Gln Asn Arg Ser Ala Arg Ile Ala Lys Gln Leu Glu Asn Asp Thr Arg
            260                 265                 270

Ile Ile Glu Val Leu Cys Lys Glu His Glu Cys Asn Ile Asp Glu Val
        275                 280                 285

Lys Asn Val Tyr Phe Lys Asn Phe Ile Pro Phe Met Asn Ser Leu Gly
    290                 295                 300

Leu Val Thr Ser Asn Gly Leu Pro Glu Val Glu Asn Leu Ser Lys Arg
305                 310                 315                 320

Tyr Glu Glu Ile Tyr Leu Lys Asn Lys Asp Leu Asp Ala Arg Leu Phe
                325                 330                 335

Leu Asp His Asp Lys Thr Leu Gln Thr Asp Ser Ile Asp Ser Phe Glu
            340                 345                 350

Thr Gln Arg Thr Pro Arg Lys Ser Asn Leu Asp Glu Glu Val Asn Val
        355                 360                 365

Ile Leu Pro His Thr Pro Val Arg Thr Val Met Asn Thr Ile Gln Gln
    370                 375                 380

Leu Met Met Ile Leu Asn Ser Ala Ser Asp Gln Pro Ser Glu Asn Leu
385                 390                 395                 400

Ile Ser Tyr Phe Asn Asn Cys Thr Val Asn Pro Lys Glu Ser Ile Leu
                405                 410                 415

Lys Arg Val Lys Asp Ile Gly Tyr Ile Phe Lys Glu Lys Phe Ala Lys
            420                 425                 430

Ala Val Gly Gln Gly Cys Val Glu Ile Gly Ser Gln Arg Tyr Lys Leu
        435                 440                 445

Gly Val Arg Leu Tyr Tyr Arg Val Met Glu Ser Met Leu Lys Ser Glu
    450                 455                 460

Glu Glu Arg Leu Ser Ile Gln Asn Phe Ser Lys Leu Leu Asn Asp Asn
465                 470                 475                 480

Ile Phe His Met Ser Leu Leu Ala Cys Ala Leu Glu Val Val Met Ala
                485                 490                 495

Thr Tyr Ser Arg Ser Thr Ser Gln Asn Leu Asp Ser Gly Thr Asp Leu
            500                 505                 510

Ser Phe Pro Trp Ile Leu Asn Val Leu Asn Leu Lys Ala Phe Asp Phe
        515                 520                 525

Tyr Lys Val Ile Glu Ser Phe Ile Lys Ala Glu Gly Asn Leu Thr Arg
    530                 535                 540

Glu Met Ile Lys His Leu Glu Arg Cys Glu His Arg Ile Met Glu Ser
545                 550                 555                 560
```

-continued

Leu Ala Trp Leu Ser Asp Ser Pro Leu Phe Asp Leu Ile Lys Gln Ser
565 570 575

Lys Asp Arg Glu Gly Pro Thr Asp His Leu Glu Ser Ala Cys Pro Leu
580 585 590

Asn Leu Pro Leu Gln Asn Asn His Thr Ala Ala Asp Met Tyr Leu Ser
595 600 605

Pro Val Arg Ser Pro Lys Lys Lys Gly Ser Thr Thr Arg Val Asn Ser
610 615 620

Thr Ala Asn Ala Glu Thr Gln Ala Thr Ser Ala Phe Gln Thr Gln Lys
625 630 635 640

Pro Leu Lys Ser Thr Ser Leu Ser Leu Phe Tyr Lys Lys Val Tyr Arg
645 650 655

Leu Ala Tyr Leu Arg Leu Asn Thr Leu Cys Glu Arg Leu Leu Ser Glu
660 665 670

His Pro Glu Leu Glu His Ile Ile Trp Thr Leu Phe Gln His Thr Leu
675 680 685

Gln Asn Glu Tyr Glu Leu Met Arg Asp Arg His Leu Asp Gln Ile Met
690 695 700

Met Cys Ser Met Tyr Gly Ile Cys Lys Val Lys Asn Ile Asp Leu Lys
705 710 715 720

Phe Lys Ile Ile Val Thr Ala Tyr Lys Asp Leu Pro His Ala Val Gln
725 730 735

Glu Thr Phe Lys Arg Val Leu Ile Lys Glu Glu Glu Tyr Asp Ser Ile
740 745 750

Ile Val Phe Tyr Asn Ser Val Phe Met Gln Arg Leu Lys Thr Asn Ile
755 760 765

Leu Gln Tyr Ala Ser Thr Arg Pro Pro Thr Leu Ser Pro Ile Pro His
770 775 780

Ile Pro Arg Ser Pro Tyr Lys Phe Pro Ser Ser Pro Leu Arg Ile Pro
785 790 795 800

Gly Gly Asn Ile Tyr Ile Ser Pro Leu Lys Ser Pro Tyr Lys Ile Ser
805 810 815

Glu Gly Leu Pro Thr Pro Thr Lys Met Thr Pro Arg Ser Arg Ile Leu
820 825 830

Val Ser Ile Gly Glu Ser Phe Gly Thr Ser Glu Lys Phe Gln Lys Ile
835 840 845

Asn Gln Met Val Cys Asn Ser Asp Arg Val Leu Lys Arg Ser Ala Glu
850 855 860

Gly Ser Asn Pro Pro Lys Pro Leu Lys Lys Leu Arg Phe Asp Ile Glu
865 870 875 880

Gly Ser Asp Glu Ala Asp Gly Ser Lys His Leu Pro Gly Glu Ser Lys
885 890 895

Phe Gln Gln Lys Leu Ala Glu Met Thr Ser Thr Arg Thr Arg Met Gln
900 905 910

Lys Gln Lys Met Asn Asp Ser Met Asp Thr Ser Asn Lys Glu Glu Lys
915 920 925

(2) INFORMATION FOR SEQ ID NO: 9:

(i) SEQUENCE CHARACTERISTICS:
(A) LENGTH: 393 amino acids
(B) TYPE: amino acid
(C) STRANDEDNESS: <Unknown>
(D) TOPOLOGY: linear -continued (ii) MOLECULE TYPE: protein (ix) FEATURE:
(A) NAME/KEY: Protein
(B) LOCATION: 1..393
(D) OTHER INFORMATION: /note= "human p53"

(xi) SEQUENCE DESCRIPTION: SEQ ID NO: 9:

```
Met Glu Glu Pro Gln Ser Asp Pro Ser Val Glu Pro Pro Leu Ser Gl
1               5                   10                  15

Glu Thr Phe Ser Asp Leu Trp Lys Leu Leu Pro Glu Asn Asn Val Le
            20                  25                  30

Ser Pro Leu Pro Ser Gln Ala Met Asp Asp Leu Met Leu Ser Pro As
        35                  40                  45

Asp Ile Glu Gln Trp Phe Thr Glu Asp Pro Gly Pro Asp Glu Ala Pr
    50                  55                  60

Arg Met Pro Glu Ala Ala Pro Pro Val Ala Pro Ala Pro Ala Ala Pr
65                  70                  75                  80

Thr Pro Ala Ala Pro Ala Pro Ala Pro Ser Trp Pro Leu Ser Ser Se
                85                  90                  95

Val Pro Ser Gln Lys Thr Tyr Gln Gly Ser Tyr Gly Phe Arg Leu Gl
            100                 105                 110

Phe Leu His Ser Gly Thr Ala Lys Ser Val Thr Cys Thr Tyr Ser Pr
        115                 120                 125

Ala Leu Asn Lys Met Phe Cys Gln Leu Ala Lys Thr Cys Pro Val Gl
    130                 135                 140

Leu Trp Val Asp Ser Thr Pro Pro Pro Gly Thr Arg Val Arg Ala Me
145                 150                 155                 160

Ala Ile Tyr Lys Gln Ser Gln His Met Thr Glu Val Val Arg Arg Cy
                165                 170                 175

Pro His His Glu Arg Cys Ser Asp Ser Asp Gly Leu Ala Pro Pro Gl
            180                 185                 190

His Leu Ile Arg Val Glu Gly Asn Leu Arg Val Glu Tyr Leu Asp As
        195                 200                 205

Arg Asn Thr Phe Arg His Ser Val Val Val Pro Tyr Glu Pro Pro Gl
    210                 215                 220

Val Gly Ser Asp Cys Thr Thr Ile His Tyr Asn Tyr Met Cys Asn Se
225                 230                 235                 240

Ser Cys Met Gly Gly Met Asn Arg Arg Pro Ile Leu Thr Ile Ile Th
                245                 250                 255

Leu Glu Asp Ser Ser Gly Asn Leu Leu Gly Arg Asn Ser Phe Glu Va
            260                 265                 270

Arg Val Cys Ala Cys Pro Gly Arg Asp Arg Arg Thr Glu Glu Glu As
        275                 280                 285

Leu Arg Lys Lys Gly Glu Pro His His Glu Leu Pro Pro Gly Ser Th
    290                 295                 300

Lys Arg Ala Leu Pro Asn Asn Thr Ser Ser Ser Pro Gln Pro Lys Ly
305                 310                 315                 320

Lys Pro Leu Asp Gly Glu Tyr Phe Thr Leu Gln Ile Arg Gly Arg Gl
                325                 330                 335

Arg Phe Glu Met Phe Arg Glu Leu Asn Glu Ala Leu Glu Leu Lys As
            340                 345                 350

Ala Gln Ala Gly Lys Glu Pro Gly Gly Ser Arg Ala His Ser Ser Hi
        355                 360                 365
```

-continued

```
Leu Lys Ser Lys Lys Gly Gln Ser Thr Ser Arg His Lys Lys Leu Me
    370                 375                 380

Phe Lys Thr Glu Gly Pro Asp Ser Asp
385                 390
```

RECOMBINANT ADENOVIRAL VECTOR AND METHOD OF USE

This application is a continuation of U.S. Ser. No. 08/328,673, filed Oct. 25, 1994, now U.S. Pat. No. 6,210,939 which is a continuation-in-part of U.S. Ser. No. 08/246,006, filed May 19, 1994, now abandoned, which is a continuation-in-part of U.S. Ser. No. 08/142,669, filed Oct. 25, 1993, now abandoned, the contents of which are hereby incorporated by reference into the present disclosure.

BACKGROUND OF THE INVENTION

Throughout this application, various publications are referred to by citations within parentheses and in the bibliographic description, immediately preceding the claims. The disclosures of these publications are hereby incorporated by reference into the present disclosure to more fully describe the state of the art to which this invention pertains.

Production of recombinant adenoviruses useful for gene therapy requires the use of a cell line capable of supplying in trans the gene products of the viral E1 region which are deleted in these recombinant viruses. At present the only useful cell line available is the 293 cell line originally described by Graham et al. in 1977. 293 cells contain approximately the left hand 12% (4.3 kb) of the adenovirus type 5 genome (Aiello (1979) and Spector (1983)).

Adenoviral vectors currently being tested for gene therapy applications typically are deleted for Ad2 or Ad5 DNA extending from approximately 400 base pairs from the 5' end of the viral genome to approximately 3.3 kb from the 5' end, for a total E1 deletion of 2.9 kb. Therefore, there exists a limited region of homology of approximately 1 kb between the DNA sequence of the recombinant virus and the Ad5 DNA within the cell line. This homology defines a region of potential recombination between the viral and cellular adenovirus sequences. Such a recombination results in a phenotypically wild-type virus bearing the Ad5 E1 region from the 293 cells. This recombination event presumably accounts for the frequent detection of wild-type adenovirus in preparations of recombinant virus and has been directly demonstrated to be the cause of wild-type contamination of the Ad2 based recombinant virus Ad2/CFTR-1 (Rich et al. (1993)).

Due to the high degree of sequence homology within the type C adenovirus subgroup such recombination is likely to occur if the vector is based on any group C adenovirus (types 1, 2, 5, 6).

In small scale production of recombinant adenoviruses, generation of contaminating wild-type virus can be managed by a screening process which discards those preparations of virus found to be contaminated. As the scale of virus production grows to meet expected demand for genetic therapeutics, the likelihood of any single lot being contaminated with a wild-type virus also will rise as well as the difficulty in providing non-contaminated recombinant preparations.

There will be over one million new cases of cancer diagnosed this year, and half that number of cancer-related deaths (American Cancer Society, 1993). p53 mutations are the most common genetic alteration associated with human cancers, occurring in 50–60% of human cancers (Hollstein et al. (1991); Bartek et al. (1991); Levine (1993)). The goal of gene therapy in treating p53 deficient tumors, for example, is to reinstate a normal, functional copy of the wild-type p53 gene so that control of cellular proliferation is restored. p53 plays a central role in cell cycle progression, arresting growth so that repair or apoptisis can occur in response to DNA damage. Wild-type p53 has recently been identified as a necessary component for apoptosis induced by irradiation or treatment with some chemotherapeutic agents (Lowe et al. (1993) A and B). Due to the high prevalence of p53 mutations in human tumors, it is possible that tumors which have become refractory to chemotherapy and irradiation treatments may have become so due in part to the lack of wild-type p53. By resupplying functional p53 to these tumors, it is reasonable that they now are susceptible to apoptisis normally associated with the DNA damage induced by radiation and chemotherapy.

One of the critical points in successful human tumor suppressor gene therapy is the ability to affect a significant fraction of the cancer cells. The use of retroviral vectors has been largely explored for this purpose in a variety of tumor models. For example, for the treatment of hepatic malignancies, retroviral vectors have been employed with little success because these vectors are not able to achieve the high level of gene transfer required for in vivo gene therapy (Huber, B. E. et al., 1991; Caruso M. et al., 1993).

To achieve a more sustained source of virus production, researchers have attempted to overcome the problem associated with low level of gene transfer by direct injection of retroviral packaging cell lines into solid tumors (Caruso, M. et al., 1993; Ezzidine, Z. D. et al., 1991; Culver, K. W. et al., 1992). However, these methods are unsatisfactory for use in human patients because the method is troublesome and induces an inflammatory response against the packaging cell line in the patient. Another disadvantage of retroviral vectors is that they require dividing cells to efficiently integrate and express the recombinant gene of interest (Huber, B. E. 1991). Stable integration into an essential host gene can lead to the development or inheritance of pathogenic diseased states.

Recombinant adenoviruses have distinct advantages over retroviral and other gene delivery methods (for review, see Siegfried (1993)). Adenoviruses have never been shown to induce tumors in humans and have been safely used as live vaccines (Straus (1984)). Replication deficient recombinant adenoviruses can be produced by replacing the E1 region necessary for replication with the target gene. Adenovirus does not integrate into the human genome as a normal consequence of infection, thereby greatly reducing the risk of insertional mutagenesis possible with retrovirus or adeno-associated viral (AAV) vectors. This lack of stable integration also leads to an additional safety feature in that the transferred gene effect will be transient, as the extrachromosomal DNA will be gradually lost with continued division of normal cells. Stable, high titer recombinant adenovirus can be produced at levels not achievable with retrovirus or AAV, allowing enough material to be produced to treat a large patient population. Moreover, adenovirus vectors are capable of highly efficient in vivo gene transfer into a broad range of tissue and tumor cell types. For example, others have shown that adenovirus mediated gene delivery has a strong potential for gene therapy for diseases such as cystic fibrosis (Rosenfeld et al. (1992); Rich et al. (1993)) and $\alpha_1$-antitrypsin deficiency (Lemarchand et al. (1992)). Although other alternatives for gene delivery, such as cationic liposome/DNA complexes, are also currently being explored, none as yet appear as effective as adenovirus mediated gene delivery.

As with treating p53 deficient tumors, the goal of gene therapy for other tumors is to reinstate control of cellular proliferation. In the case of p53, introduction of a functional gene reinstates cell cycle control allowing for apoptotic cell death induced by therapeutic agents. Similarly, gene therapy is equally applicable to other tumor suppressor genes which can be used either alone or in combination with therapeutic agents to control cell cycle progression of tumor cells and/or induce cell death. Moreover, genes which do not encode cell cycle regulatory proteins, but directly induce cell death such as suicide genes or, genes which are directly toxic to the cell can be used in gene therapy protocols to directly eliminate the cell cycle progression of tumor cells.

Regardless of which gene is used to reinstate the control of cell cycle progression, the rationale and practical applicability of this approach is identical. Namely, to achieve high efficiencies of gene transfer to express therapeutic quantities of the recombinant product. The choice of which vector to use to enable high efficiency gene transfer with minimal risk to the patient is therefore important to the level of success of the gene therapy treatment.

Thus, there exists a need for vectors and methods which provide high level gene transfer efficiencies and protein expression which provide safe and effective gene therapy treatments. The present invention satisfies this need and provides related advantages as well.

SUMMARY OF THE INVENTION

This invention provides a recombinant adenovirus expression vector characterized by the partial or total deletion of the adenoviral protein IX DNA and having a gene encoding a foreign protein or a functional fragment or mutant thereof. Transformed host cells and a method of producing recombinant proteins and gene therapy also are included within the scope of this invention.

Thus, for example, the adenoviral vector of this invention can contain a foreign gene for the expression of a protein effective in regulating the cell cycle, such as p53, Rb, or mitosin, or in inducing cell death, such as the conditional suicide gene thymidine kinase. (The latter must be used in conjunction with a thymidine kinase metabolite in order to be effective).

BRIEF DESCRIPTION OF THE FIGURES

FIGS. 2A through 2D show the amino acid sequence of $p110^{RB}$ (SEQ ID NO: 8).

FIGS. 3A through 3D show a DNA sequence encoding a retinoblastoma tumor suppressor protein (SEQ ID NOS: 7–8).

In FIG. 8A, the plasmid pACNTK was constructed by subcloning the HSV-TK gene from pMLBKTK (ATCC No. 39369) into the polylinker of a cloning vector, followed by isolation of the TK gene with the desired ends for cloning into the pACN vector. The pACN vector contains adenoviral sequences necessary for in vivo recombination to occur to form recombinant adenovirus (see FIG. 9). In FIG. 8B, the construction of the plasmid pAANTK is shown beginning with PCR amplified fragments encoding the α-fetoprotein enhancer (AFP-E) and promoter (AFP-P) regions subcloned through several steps into a final plasmid where the AFP enhancer and promoter are upstream of the HSV-TK gene followed by adenovirus Type 2 sequences necessary for in vivo recombination to occur to form recombinant adenovirus. In FIG. 8C, the construction of the plasmid pAANCAT is shown beginning with the isolation of the chloramphenicol acetyltransferase (CAT) gene from a commercially available plasmid and subcloning it into the pAAN plasmid (see above), generating the final plasmid pAANCAT where the AFP enhancer/promoter direct transcription of the CAT gene in an adenovirus sequence background.

In FIG. 12A, tumor sizes are plotted for each virus versus days post infection (mean+/−SEM). In FIG. 12B, body weight for each virus-treated animal group is plotted as the mean+/−SEM versus days post infection.

DETAILED DESCRIPTION OF THE INVENTION

To reduce the frequency of contamination with wild-type adenovirus, it is desirable to improve either the virus or the cell line to reduce the probability of recombination. For example, an adenovirus from a group with low homology to the group C viruses could be used to engineer recombinant viruses with little propensity for recombination with the Ads sequences in 293 cells. However, an alternative, easier means of reducing the recombination between viral and cellular sequences is to increase the size of the deletion in the recombinant virus and thereby reduce the extent of shared sequence between it and the Ad5 genes in the 293 cells.

Deletions which extend past 3.5 kb from the 5' end of the adenoviral genome affect the gene for adenoviral protein IX and have not been considered desirable in adenoviral vectors (see below).

The protein IX gene of the adenoviruses encodes a minor component of the outer adenoviral capsid which stabilizes the group-of-nine hexons which compose the majority of the viral capsid (Stewart (1993)). Based upon study of adenovirus deletion mutants, protein IX initially was thought to be a non-essential component of the adenovirus, although its absence was associated with greater heat lability than observed with wild-type virus (Colby and Shenk (1981)). More recently it was discovered that protein IX is essential for packaging full length viral DNA into capsids and that in the absence of protein IX, only, genomes at least 1 kb smaller than wild-type could be propagated as recombinant viruses (Ghosh-Choudhury et al. (1987)). Given this packaging limitation, protein IX deletions deliberately have not been considered in the design of adenoviral vectors.

In this application, reference is made to standard textbooks of molecular biology that contain definitions, methods and means for carrying out basic techniques, encompassed by the present invention. See for example, Sambrook et al. (1989) and the various references cited therein. This reference and the cited publications are expressly incorporated by reference into this disclosure.

Figure 1A:
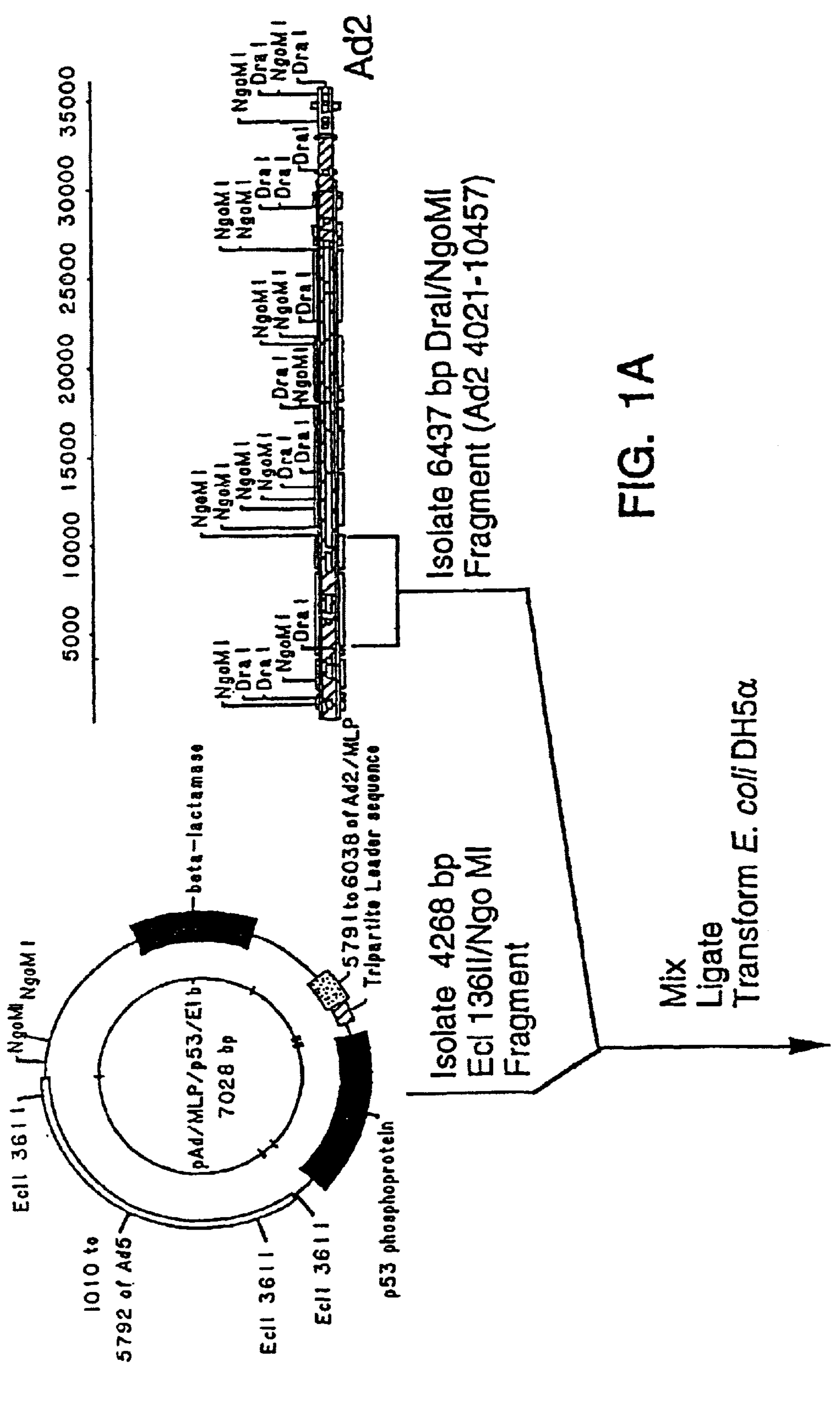
FIGS. 1A and 1B show a recombinant adenoviral vector of this invention. This construct was assembled as shown in FIGS. 1A and 1B. The resultant virus bears a 5' deletion of adenoviral sequences extending from nucleotide 356 to 4020 and eliminates the E1a and E1b genes as well as the entire protein IX coding sequence, leaving the polyadenylation site shared by the E1b and pIX genes intact for use in terminating transcription of any desired gene.
Figure 1B:
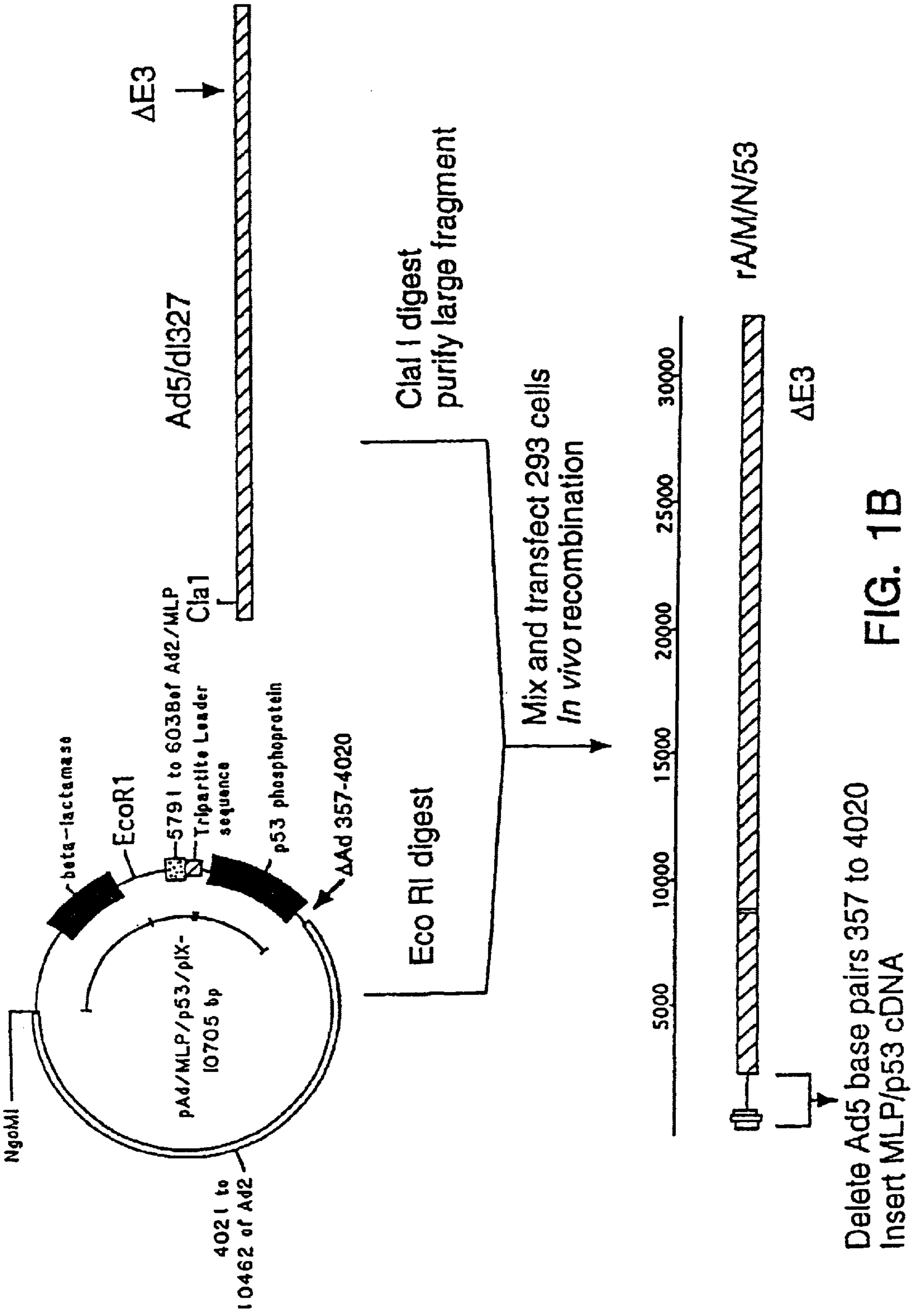
Figure 4:
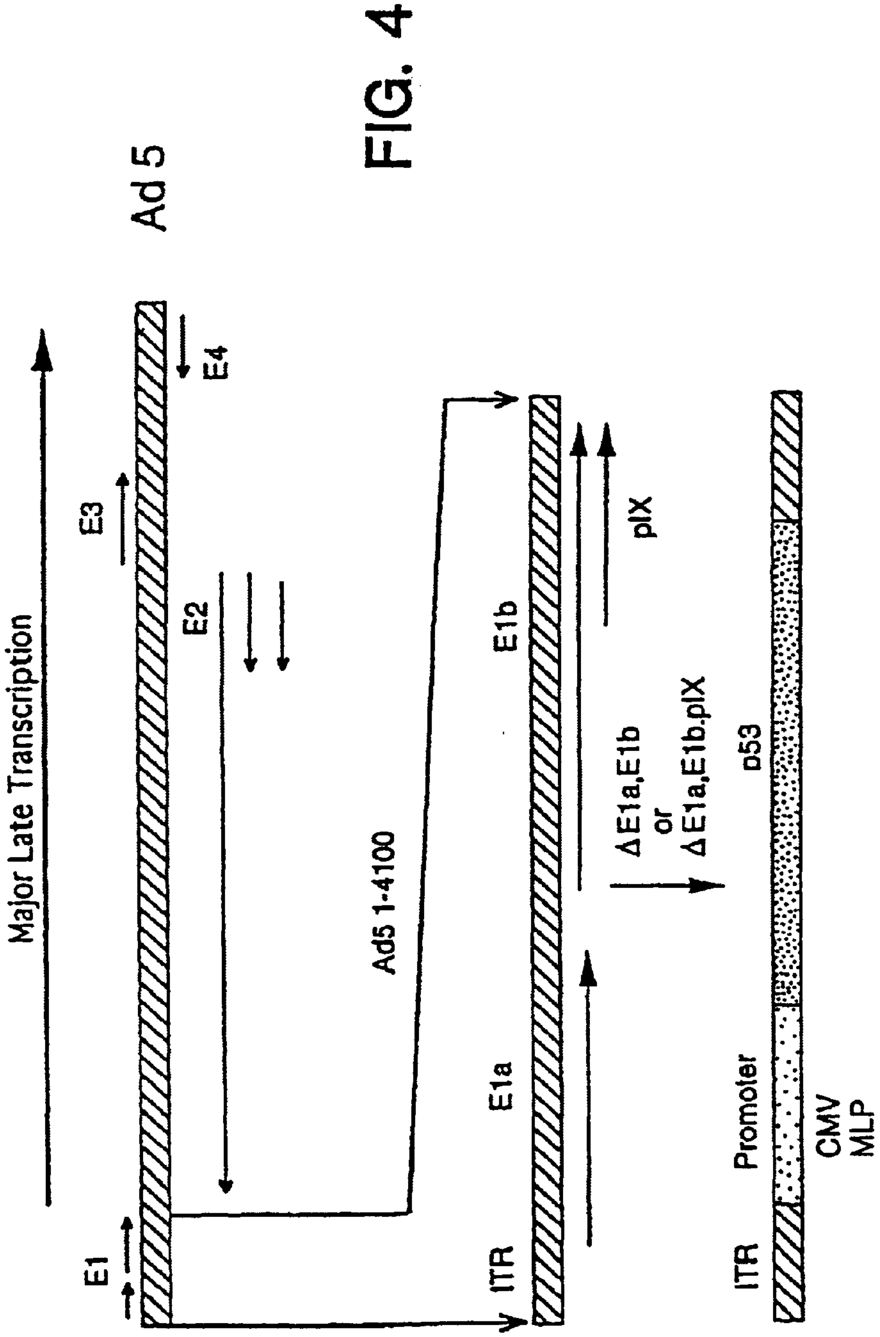
FIG. 4 shows schematic of recombinant p53/adenovirus constructs within the scope of this invention. The p53 recombinants are based on Ad 5 and have had the E1 region of nucleotides 360–3325 replaced with a 1.4 kb full length p53 cDNA driven by the Ad 2 MLP (A/M/53) or human CMV (A/C/53) promoters followed by the Ad 2 tripartite leader cDNA. The control virus A/M has the same Ad 5 deletions as the A/M/53 virus but lacks the 1.4 kb p53 cDNA insert. The remaining E1b sequence (705 nucleotides) have been deleted to create the protein IX deleted constructs A/M/N/53 and A/C/N/53. These constructs also have a 1.9 kb Xba I deletion within adenovirus type 5 region E3.
Figure 5A:
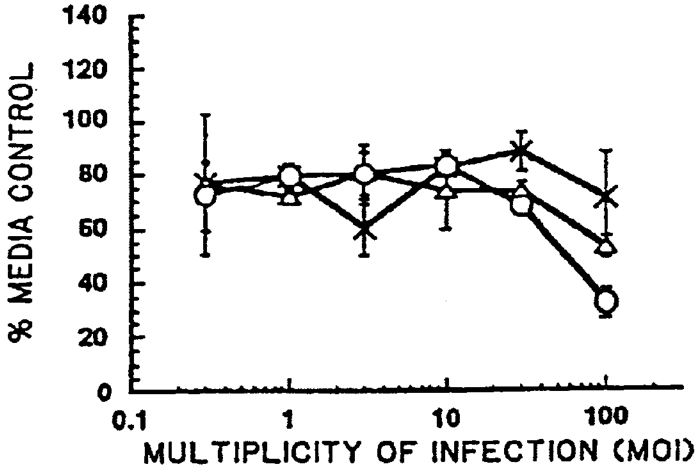
FIGS. 5A through 5I show p53 dependent inhibition of DNA synthesis in nine different human tumor cell lines by A/M/N/53 and A/C/N/53. Nine different tumor cell lines were infected with either control adenovirus A/M (-x-x-), or the p53 expressing A/M/N/53 (-Δ-Δ-), or A/C/N/53 (-O-O-) virus at increasing MOI as indicated. The tumor type and p53 status is noted for each cell line (wt=wild type, null=no protein expressed, mut=mutant protein expressed). DNA synthesis was measured 72 hours post-infection as described below in Experiment No. II. Results are from triplicate measurements at each dose (mean+/−SD), and are plotted as % of media control versus MOI. * H69 cells were only tested with A/M and A/M/N/53 virus.
Figure 5B:
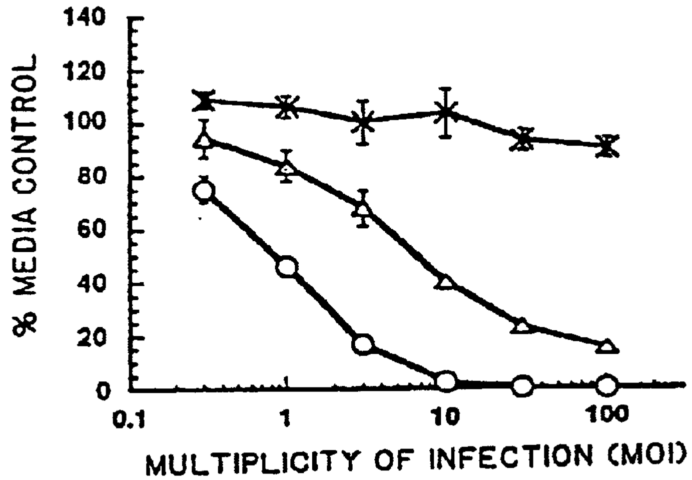
Figure 5C:
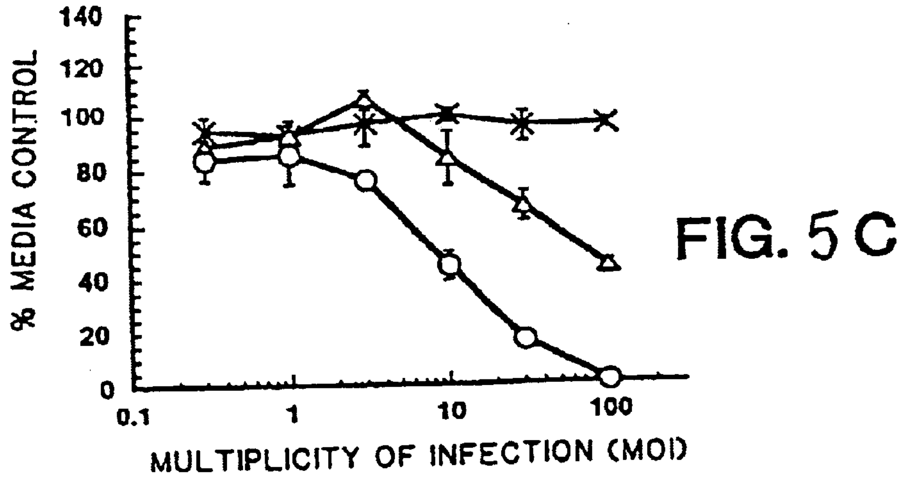
Figure 5D:
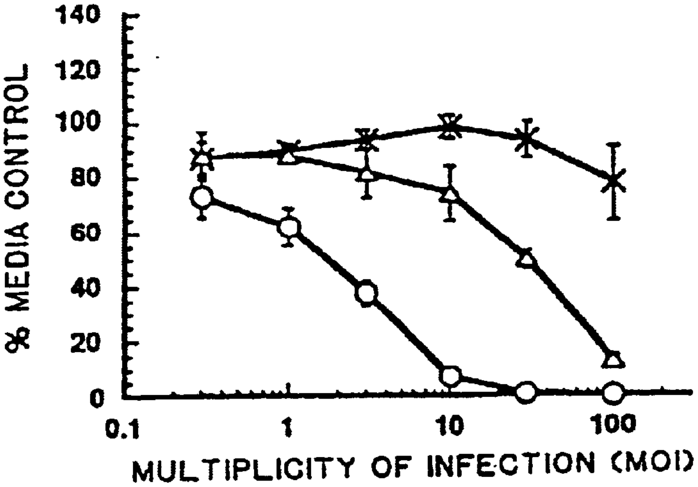
Figure 5E:
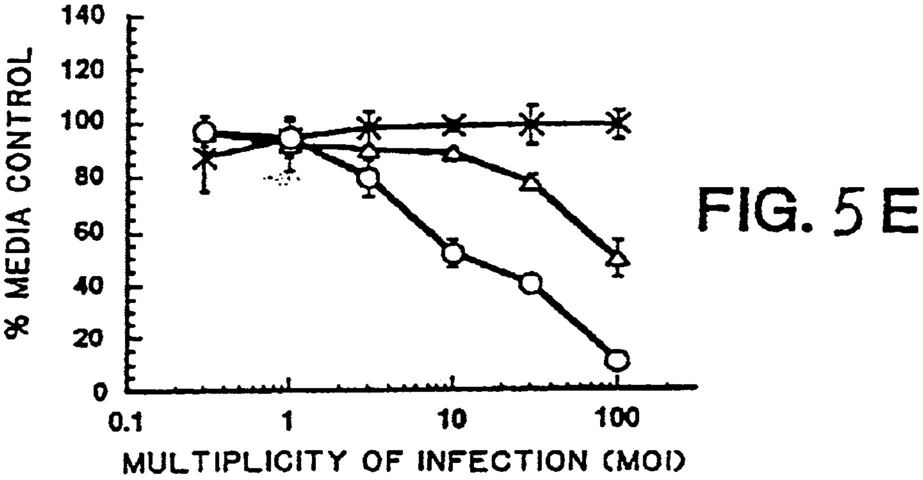
Figure 5F:
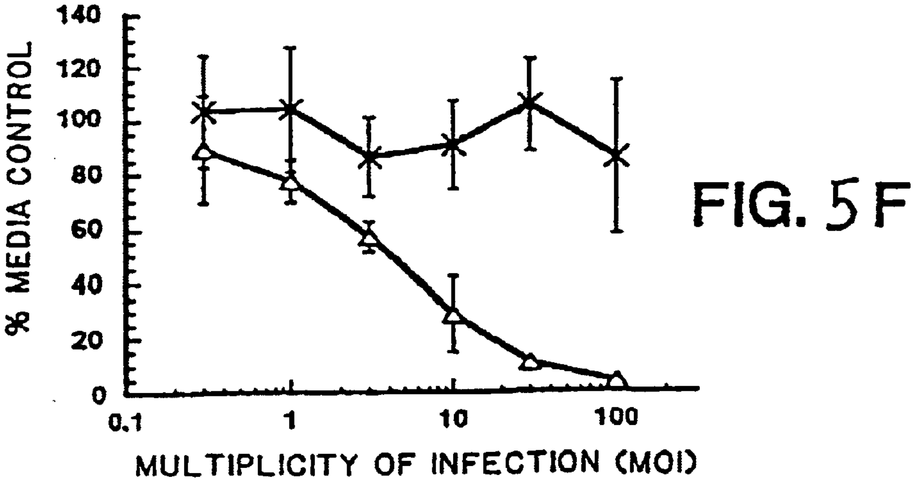
Figure 5G:
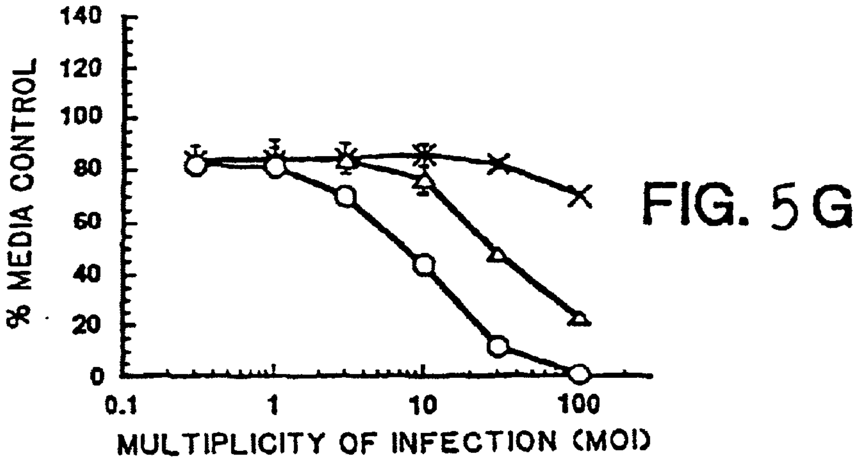
Figure 5H:
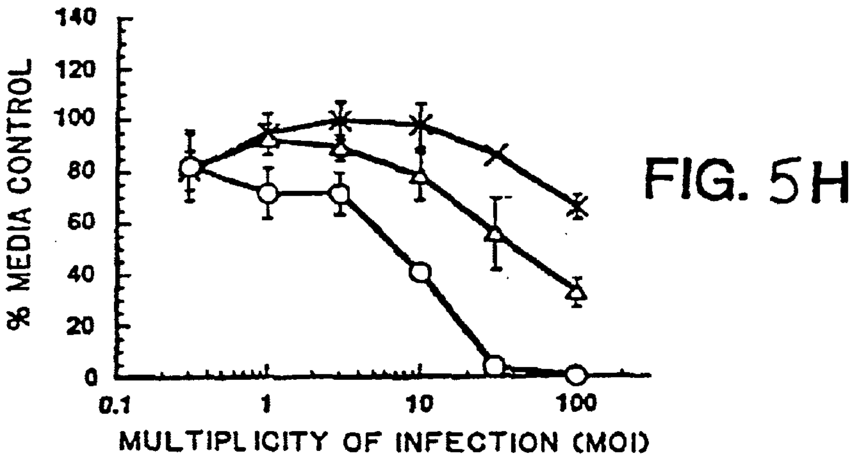
Figure 5I:
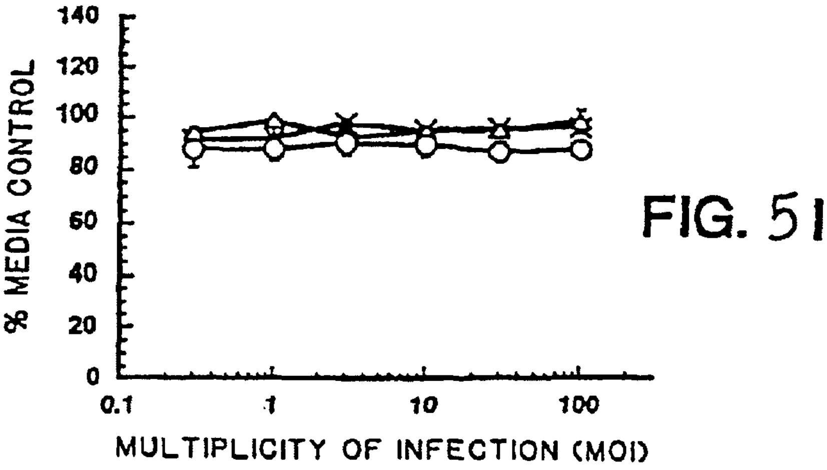

Contrary to what has been known in the art, this invention claims the use of recombinant adenoviruses bearing deletions of the protein IX gene as a means of reducing the risk of wild-type adenovirus contamination in virus preparations for use in diagnostic and therapeutic applications such as gene therapy. As used herein, the term "recombinant" is intended to mean a progeny formed as the result of genetic engineering. These deletions can remove an additional 500 to 700 base pairs of DNA sequence that is present in conventional E1 deleted viruses (smaller, less desirable, deletions of portions of the pIX gene are possible and are included within the scope of this invention) and is available for recombination with the Ad5 sequences integrated in 293 cells. Recombinant adenoviruses based on any group C virus, serotype 1, 2, 5 and 6, are included in this invention. Also encompassed by this invention is a hybrid Ad2/Ad5 based recombinant virus expressing the human p53 cDNA from the adenovirus type 2 major late promoter. This construct was assembled as shown in FIG. 1. The resultant virus bears a 5' deletion of adenoviral sequences extending from about nucleotide 357 to 4020 and eliminates the E1a and E1b genes as well as the entire protein IX coding sequence, leaving the polyadenylation site shared by the E1b and protein IX genes intact for use in terminating transcription of any desired gene. A separate embodiment is shown in FIG. 4. Alternatively, the deletion can be extended an additional 30 to 40 base pairs without affecting the adjacent gene for protein IVa2, although in that case an exogenous polyadenylation signal is provided to terminate transcription of genes inserted into the recombinant virus. The initial virus constructed with this deletion is easily propagated in 293 cells with no evidence of wild-type viral contamination and directs robust p53 expression from the transcriptional unit inserted at the site of the deletion.

The insert capacity of recombinant viruses bearing the protein IX deletion described above is approximately 2.6 kb. This is sufficient for many genes including the p53 cDNA. Insert capacity can be increased by introducing other deletions into the adenoviral backbone, for example, deletions within early regions 3 or 4 (for review see: Graham and Prevec (1991)). For example, the use of an adenoviral backbone containing a 1.9 kb deletion of non-essential sequence within early region 3. With this additional deletion, the insert capacity of the vector is increased to approximately 4.5 kb, large enough for many larger cDNAs, including that of the retinoblastoma tumor suppressor gene.

A recombinant adenovirus expression vector characterized by the partial or total deletion of the adenoviral protein IX DNA and having a gene encoding a foreign protein, or a functional fragment or mutant thereof is provided by this invention. These vectors are useful for the safe recombinant production of diagnostic and therapeutic polypeptides and proteins, and more importantly, for the introduction of genes in gene therapy. Thus, for example, the adenoviral vector of this invention can contain a foreign gene for the expression of a protein effective in regulating the cell cycle, such as p53, Rb, or mitosin, or in inducing cell death, such as the conditional suicide gene thymidine kinase. (The latter must be used in conjunction with a thymidine kinase metabolite in order to be effective) Any expression cassette can be used in the vectors of this invention. An "expression cassette" means a DNA molecule having a transcription promoter/enhancer such as the CMV promotor enhancer, etc., a foreign gene, and in some embodiments defined below, a polyadentlyation signal. As used herein, the term "foreign gene" is intended to mean a DNA molecule not present in the exact orientation and position as the counterpart DNA molecule found in wild-type adenovirus. The foreign gene is a DNA molecule up to 4.5 kilobases. "Expression vector" means a vector that results in the expression of inserted DNA sequences when propagated in a suitable host cell, i.e., the protein or polypeptide coded for by the DNA is synthesized by the host's system. The recombinant adenovirus expression vector can contain part of the gene encoding adenovirus protein IX, provided that biologically active protein IX or fragment thereof is not produced. Example of this vector are an expression vector having the restriction enzyme map of FIGS. 1 or 4.

Inducible promoters also can be used in the adenoviral vector of this invention. These promoters will initiate transcription only in the presence of an additional molecule. Examples of inducible promoters include those obtainable from a β-interferon gene, a heat shock gene, a metallothionine gene or those obtainable from steroid hormone-responsive genes. Tissue specific expression has been well characterized in the field of gene expression and tissue specific and inducible promoters such as these are very well known in the art. These genes are used to regulate the expression of the foreign gene after it has been introduced into the target cell.

Also provided by this invention is a recombinant adenovirus expression vector, as described above, having less extensive deletions of the protein IX gene sequence extending from 3500 bp from the 5' viral termini to approximately 4000 bp, in one embodiment. In a separate embodiment, the recombinant adenovirus expression vector can have a further deletion of a non-essential DNA sequence in adenovirus early region 3 and/or 4 and/or deletion of the DNA sequences designated adenovirus E1a and E1b. In this embodiment, foreign gene is a DNA molecule of a size up to 4.5 kilobases.

A further embodiment has a deletion of up to forty nucleotides positioned 3' to the E1a and E1b deletion and pIX and a foreign DNA molecule encoding a polyadenylation signal inserted into the recombinant vector in a position relative to the foreign gene to regulate the expression of the foreign gene.

For the purposes of this invention, the recombinant adenovirus expression vector can be derived from wild-type group adenovirus, serotype 1, 2, 5 or 6.

In one embodiment, the recombinant adenovirus expression vector has a foreign gene coding for a functional tumor suppressor protein, or a biologically active fragment thereof. As used herein, the term "functional" as it relates to a tumor suppressor gene, refers to tumor suppressor genes that encode tumor suppressor proteins that effectively inhibit a cell from behaving as a tumor cell. Functional genes can include, for instance, wild type of normal genes and modifications of normal genes that retains its ability to encode effective tumor suppressor proteins and other anti-tumor genes such as a conditional suicide protein or a toxin.

Similarly, "non-functional" as used herein is synonymous with "inactivated." Non-functional or defective genes can be caused by a variety of events, including for example point mutations, deletions, methylation and others known to those skilled in the art.

As used herein, an "active fragment" of a gene includes smaller portions of the gene that retain the ability to encode proteins having tumor suppressing activity. $p56^{RB}$, described more fully below, is but one example of an active fragment of a functional tumor suppressor gene. Modifications of tumor suppressor genes are also contemplated within the meaning of an active fragment, such as additions, deletions or substitutions, as long as the functional activity of the unmodified gene is retained.

Another example of a tumor suppressor gene is retinoblastoma (RB). The complete RB cDNA nucleotide sequences and predicted amino acid sequences of the resulting RB protein (designated $p110^{RB}$) are shown in Lee et al. (1987) and in FIGS. 3A through 3D (SEQ ID NOS: 7–8). Also useful to express retinoblastoma tumor suppressor protein is a DNA molecule encoding the amino acid sequence shown in FIGS. 2A through 2D (SEQ ID NO: 8) or having the DNA sequence shown in FIGS. 3A through 3D (SEQ ID NOS: 7–8). A truncated version of $p110^{RB}$, called $p56^{RB}$ also is useful. For the sequence of $p56^{RB}$, see Huang et al. (1991). Additional tumor suppressor genes can be used in the vectors of this invention. For illustration purposes only, these can be p16 protein (Kamb et al. (1994)), p21 protein, Wilm's tumor WT1 protein, mitosin, h-NUC, or colon carcinoma DCC protein. Mitosin is described in X. Zhu and W-H Lee, U.S. patent application Ser. No. 08/141,239, filed Oct. 22, 1993, and a subsequent continuation-in-part by the same inventors, attorney docket number P-CJ 1191, filed Oct. 24, 1994, both of which are herein incorporated by reference. Similarly, h-NUC is described by W-H Lee and P-L Chen, U.S. patent application Ser. No. 08/170,586, filed Dec. 20, 1993, herein incorporated by reference.

As is known to those of skill in the art, the term "protein" means a linear polymer of amino acids joined in a specific sequence by peptide bonds. As used herein, the term "amino acid" refers to either the D or L stereoisomer form of the amino acid, unless otherwise specifically designated. Also encompassed within the scope of this invention are equivalent proteins or equivalent peptides, e.g., having the biological activity of purified wild type tumor suppressor protein. "Equivalent proteins" and "equivalent polypeptides" refer to compounds that depart from the linear sequence of the naturally occurring proteins or polypeptides, but which have amino acid substitutions that do not change its biologically activity. These equivalents can differ from the native sequences by the replacement of one or more amino acids with related amino acids, for example, similarly charged amino acids, or the substitution or modification of side chains or functional groups.

Also encompassed within the definition of a functional tumor suppressor protein is any protein whose presence reduces the tumorigenicity, malignancy or hyperproliferative phenotype of the host cell. Examples of tumor suppressor proteins within this definition include, but are not limited to p110$^{RB}$, p56$^{RB}$, mitosin, h-NUC and p53. "Tumorigenicity" is intended to mean having the ability to form tumors or capable of causing tumor formation and is synonymous with neoplastic growth. "Malignancy" is intended to describe a tumorigenic cell having the ability to metastasize and endanger the life of the host organism. "Hyperproliferative phenotype" is intended to describe a cell growing and dividing at a rate beyond the normal limitations of growth for that cell type. "Neoplastic" also is intended to include cells lacking endogenous functional tumor suppressor protein or the inability of the cell to express endogenous nucleic acid encoding a functional tumor suppressor protein.

An example of a vector of this invention is a recombinant adenovirus expression vector having a foreign gene coding for p53 protein or an active fragment thereof is provided by this invention. The amino acid sequence encoded by the p53 gene is set forth below in Table 1 (SEQ ID NO: 9).

TABLE 1

```
                                                            50
                                                         MEEPQ

                                                           100
SDPSV EPPLS QETFS DLWKL LPENN VLSPL PSQAM DDLML SPDDI EQWFT

                                                           150
EDPGP DEAPR MPEAA PPVAP APAAP TPAAP APAPS WPLSS SVPSQ KTYQG

                                                           200
SYGFR LGFLH SGTAK SVTCT YSPAL NKMFC QLAKT CPVQL WVDST PPPGT

                                                           250
RVRAM AIYKQ SQHMT EVVRR CPHHE RCSDS DGLAP PQHLI RVEGN LRVEY

                                                           300
LDDRN TFRHS VVVPY EPPEV GSDCT TIHYN YMCNS SCMGG MNRRP ILTII

                                                           350
TLEDS SGNLL GRNSF EVRVC ACPGR DRRTE EENLR KKGEP HHELP PGSTK

                                                           400
RALPN NTSSS PQPKK KPLDG EYFTL QIRGR ERFEM FRELN EALEL KDAQA

GKEPG GSRAH SSHLK SKKGQ STSRH KKLMF KTEGP DSD*
```

* = Stop codon

Any of the expression vectors described herein are useful as compositions for diagnosis or therapy. The vectors can be used for screening which of many tumor suppressor genes would be useful in gene therapy. For example, a sample of cells suspected of being neoplastic can be removed from a subject and mammal. The cells can then be contacted, under suitable conditions and with an effective amount of a recombinant vector of this invention having inserted therein a foreign gene encoding one of several functional tumor suppressor genes. Whether the introduction of this gene will reverse the malignant phenotype can be measured by colony formation in soft agar or tumor formation in nude mice. If the malignant phenotype is reversed, then that foreign gene is determined to be a positive candidate for successful gene therapy for the subject or mammal. When used pharmaceutically, they can be combined with one or more pharmaceutically acceptable carriers. Pharmaceutically acceptable carriers are well known in the art and include aqueous solutions such as physiologically buffered saline or other solvents or vehicles such as glycols, glycerol, vegetable oils (eg., olive oil) or injectable organic esters. A pharmaceutically acceptable carrier can be used to administer the instant compositions to a cell in vitro or to a subject in vivo.

A pharmaceutically acceptable carrier can contain a physiologically acceptable compound that acts, for example, to stabilize the composition or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of a pharmaceutically acceptable carrier, including a physiologically acceptable compound, depends, for example, on the route of administration of the polypeptide and on the particular physiochemical characteristics of the specific polypeptide. For example, a physiologically acceptable compound such as aluminum monosterate or gelatin is particularly useful as a delaying agent, which prolongs the rate of absorption of a pharmaceutical composition administered to a subject. Further examples of carriers, stabilizers or adjutants can be found in Martin, Remington's Pharm. Sci., 15th Ed. (Mack Publ. Co., Easton, 1975), incorporated herein by reference. The pharmaceutical composition also can be incorporated, if desired, into liposomes, microspheres or other polymer matrices (Gregoriadis, Liposome Technology, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

As used herein, "pharmaceutical composition" refers to any of the compositions of matte described herein in combination with one or more of the above pharmaceutically acceptable carriers. The compositions can then be administered therapeutically or prophylactically. They can be contacted with the host cell in vivo, ex vivo, or in vitro, in an effective amount. In vitro and ex vivo means of contacting host cells are provided below. When practiced in vivo, methods of administering a pharmaceutical containing the vector of this invention, are well known in the art and include but are not limited to, administration orally, intratumorally, intravenously, intramuscularly or intraperitoneal. Administration can be effected continuously or intermittently and will vary with the subject and the condition to be treated, e.g., as is the case with other therapeutic compositions (Landmann et al. (1992); Aulitzky et al. (1991); Lantz et al. (1990); Supersaxo et al. (1988); Demetri et al. (1989); and LeMaistre et al. (1991)).

Further provided by this invention is a transformed procaryotic or eucaryotic host cell, for example an animal cell or mammalian cell, having inserted a recombinant adenovirus expression vector described above. Suitable procaryotic cells include but are not limited to bacterial cells such as *E. coli* cells. Methods of transforming host cells with retroviral vectors are known in the art, see Sambrook et al. (1989) and include, but are not limited to transfection, electroporation, and microinjection.

As used throughout this application, the term animal is intended to be synonymous with mammal and is to include, but not be limited to bovine, porcine, feline, simian, canine, equine, murine, rat or human. Additional host cells include but are not limited to any neoplastic or tumor cell, such as osteosarcoma, ovarian carcinoma, breast carcinoma, melanoma, hepatocarcinoma, lung cancer, brain cancer, colorectal cancer, hematopoietic cell, prostate cancer, cervical carcinoma, retinoblastoma, esophageal carcinoma, bladder cancer, neuroblastoma, or renal cancer.

Additionally, any eucaryotic cell line capable of expressing E1a and E1b or E1a, E1b and pIX is a suitable host for this vector. In one embodiment, a suitable eucaryotic host cell is the 293 cell line available from the American Type Culture Collection, 12301 Parklawn Drive, Rockville, Md., U.S.A. 20231.

Any of the transformed host cells described herein are useful as compositions for diagnosis or therapy. When used pharmaceutically, they can be combined with various pharmaceutically acceptable carriers. Suitable pharmaceutically acceptable carriers are well known to those of skill in the art and, for example, are described above. The compositions can then be administered therapeutically or prophylactically, in effective amounts, described in more detail below.

A method of transforming a host cell also is provided by this invention. This method provides contacting a host cell, i.e., a procaryotic or eucaryotic host cell, with any of the expression vectors described herein and under suitable conditions. Host cells transformed by this method also are claimed within the scope of this invention. The contacting can be effected in vitro, in vivo, or ex vivo, using methods well known in the art (Sambrook et al. (1989)) and using effective amounts of the expression vectors. Also provided in this invention is a method of producing a recombinant protein or polypeptide by growing the transformed host cell under suitable conditions favoring the transcription and translation of the inserted foreign gene. Methods of recombinant expression in a variety of host cells, such as mammalian, yeast, insect or bacterial cells, are widely known, including those described in Sambrook et al., supra. The translated foreign gene can then be isolated by convention means, such as column purification or purification using an anti-protein antibody. The isolated protein or polypeptide also is intended within the scope of this invention. As used herein, purified or isolated mean substantially free of native proteins or nucleic acids normally associated with the protein or polypeptide in the native or host cell environment.

Also provided by this invention are non-human animals having inserted therein the expression vectors or transformed host cells of this invention. These "transgenic" animals are made using methods well known to those of skill in the art, for example as described in U.S. Pat. No. 5,175,384 or by conventional ex vivo therapy techniques, as described in Culver et al. (1991).

As shown in detail below, the recombinant adenoviruses expressing a tumor suppressor wild-type p53, as described above, can efficiently inhibit DNA synthesis and suppress the growth of a broad range of human tumor cell types, including clinical targets. Furthermore, recombinant adenoviruses can express tumor suppression genes such as p53 in an in vivo established tumor without relying on direct injection into the tumor or prior ex vivo treatment of the cancer cells. The p53 expressed is functional and effectively suppresses tumor growth in vivo and significantly increases survival time in a nude mouse model of human lung cancer.

Thus, the vectors of this invention are particularly suited for gene therapy. Accordingly, methods of gene therapy utilizing these vectors are within the scope of this invention. The vector is purified and then an effective amount is administered in vivo or ex vivo into the subject. Methods of gene therapy are well known in the art, see, for example, Larrick, J. W. and Burck, K. L. (1991) and Kreigler, M. (1990). "Subject" means any animal, mammal, rat, murine, bovine, porcine, equine, canine, feline or human patient. When the foreign gene codes for a tumor suppressor gene or other anti-tumor protein, the vector is useful to treat or reduce hyperproliferative cells in a subject, to inhibit tumor proliferation in a subject or to ameliorate a particular related pathology. Pathologic hyperproliferative cells are characteristic of the following disease states, thyroid hyperplasia-Grave's Disease, psoriasis, benign prostatic hypertrophy, Li-Fraumeni syndrome including breast cancer, sarcomas and other neoplasms, bladder cancer, colon cancer, lung cancer, various leukemias and lymphomas. Examples of non-pathologic hyperproliferative cells are found, for instance, in mammary ductal epithelial cells during development of lactation and also in cells associated with wound repair. Pathologic hyperproliferative cells characteristically exhibit loss of contact inhibition and a decline in their ability to selectively adhere which implies a change in the surface properties of the cell and a further breakdown in intercellular communication. These changes include stimulation to divide and the ability to secrete proteolytic enzymes.

Moreover, the present invention relates to a method for depleting a suitable sample of pathologic mammalian hyperproliferative cells contaminating hematopoietic precursors during bone marrow reconstitution, via the introduction of a wild type tumor suppressor gene into the cell preparation using the vector of this invention (whether derived from autologous peripheral blood or bone marrow). As used herein, a "suitable sample" is defined as a heterogeneous cell preparation obtained from a patient, e.g., a mixed population of cells containing both phenotypically normal and pathogenic cells. "Administer" includes, but is not limited to introducing into the cell or subject intravenously, by direct injection into the tumor, by intra-tumoral injection, by intraperitoneal administration, by aerosol administration to the lung or topically. Such administration can be combined with a pharmaceutically-accepted carrier, described above.

The term "reduced tumorigenicity" is intended to mean tumor cells that have been converted into less tumorigenic or non-tumorigenic cells. Cells with reduced tumorigenicity either form no tumors in vivo or have an extended lag time of weeks to months before the appearance of in viva tumor growth and/or slower growing three dimensional tumor mass compared to tumors having fully inactivated or non-functional tumor suppressor gene.

As used herein, the term "effective amount" is intended to mean the amount of vector or anti-cancer protein which achieves a positive outcome on controlling cell proliferation. For example, one dose contains from about $10^8$ to about $10^{13}$ infectious units. A typical course of treatment would be one such dose a day over a period of five days. An effective amount will vary on the pathology or condition to be treated, by the patient and his status, and other factors well known to those of skill in the art. Effective amounts are easily determined by those of skill in the art.

Also within the scope of this invention is a method of ameliorating a pathology characterized by hyperproliferative cells or genetic defect in a subject by administering to the subject an effective amount of a vector described above containing a foreign gene encoding a gene product having the ability to ameliorate the pathology, under suitable conditions. As used herein, the term "genetic defect" means any disease or abnormality that results from inherited factors, such as sickle cell anemia or Tay-Sachs disease.

This invention also provides a method for reducing the proliferation of tumor cells in a subject by introducing into the tumor mass an effective amount of an adenoviral expression vector containing an anti-tumor gene other than a tumor suppressor gene. The anti-tumor gene can encode, for example, thymidine kinase (TK). The subject is then administered an effective amount of a therapeutic agent, which in the presence of the anti-tumor gene is toxic to the cell. In the specific case of thymidine kinase, the therapeutic agent is a thymidine kinase metabolite such as ganciclovir (GCV), 6-methoxypurine arabinonucleoside (araM), or a functional equivalent thereof. Both the thymidine kinase gene and the thymidine kinase metabolite must be used concurrently to be toxic to the host cell. However, in its presence, GCV is phosphorylated and becomes a potent inhibitor of DNA synthesis whereas araM gets converted to the cytotoxic anabolite araATP. Other anti-tumor genes can be used as well in combination with the corresponding therapeutic agent to reduce the proliferation of tumor cells. Such other gene and therapeutic agent combinations are known by one skilled in the art. Another example would be the vector of this invention expressing the enzyme cytosine deaminase. Such vector would be used in conjunction with administration of the drug 5-fluorouracil (Austin and Huber, 1993), or the recently described *E. Coli* Deo Δ gene in combination with 6-methyl-purine-2'-deosribonucleoside (Sorscher et al 1994).

As with the use of the tumor suppressor genes described previously, the use of other anti-tumor genes, either alone or in combination with the appropriate therapeutic agent provides a treatment for the uncontrolled cell growth or proliferation characteristic of tumors and malignancies. Thus, this invention provides a therapy to stop the uncontrolled cellular growth in the patient thereby alleviating the symptoms of the disease or cachexia present in the patient. The effect of this treatment includes, but is not limited to, prolonged survival time of the patient, reduction in tumor mass or burden, apoptosis of tumor cells or the reduction of the number of circulating tumor cells. Means of quantifying the beneficial effects of this therapy are well known to those of skill in the art.

The invention provides a recombinant adenovirus expression vector characterized by the partial or total deletion of the adenoviral protein IX DNA and having a foreign gene encoding a foreign protein, wherein the foreign protein is a suicide gene or functional equivalent thereof. The anti-cancer gene TK, described above, is an example of a suicide gene because when expressed, the gene product is, or can be made to be lethal to the cell. For TK, lethality is induced in the presence of GCV. The TK gene is derived from herpes simplex virus by methods well known to those of skill in the art. The plasmid pMLBKTK in *E. coli* HB101 (from ATCC #39369) is a source of the herpes simplex virus (HSV-1) thymidine kinase (TK) gene for use in this invention. However, many other sources exist as well.

The TK gene can be introduced into the tumor mass by combining the adenoviral expression vector with a suitable pharmaceutically acceptable carrier. Introduction can be accomplished by, for example, direct injection of the recombinant adenovirus into the tumor mass. For the specific case of a cancer such as hepatocellular carcinoma (HCC), direct injection into the hepatic artery can be used for delivery because most HCCs derive their circulation from this artery. To control proliferation of the tumor, cell death is induced by treating the patients with a TK metabolite such as ganciclovir to achieve reduction of tumor mass. The TK metabolite can be administered, for example, systemically, by local innoculation into the tumor or in the specific case of HCC, by injection into the hepatic artery. The TK metabolite is preferably administered at least once daily but can be increased or decreased according to the need. The TK metabolite can be administered simultaneous or subsequent to the administration of the TK containing vector. Those skilled in the art know or can determine the dose and duration which is therapeutically effective.

A method of tumor-specific delivery of a tumor suppressor gene is accomplished by contacting target tissue in an animal with an effective amount of the recombinant adenoviral expression vector of this invention. The gene is intended to code for an anti-tumor agent, such as a functional tumor suppressor gene or suicide gene. "Contacting" is intended to encompass any delivery method for the efficient transfer of the vector, such as intra-tumoral injection.

The use of the adenoviral vector of this invention to prepare medicaments for the treatment of a disease or for therapy is further provided by- this invention.

The following examples are intended to illustrate, not limit the scope of this invention.

EXPERIMENT NO. I

Plasmid pAd/MLP/p53/E1b- was used as the starting material for these manipulations. This plasmid is based on the pBR322 derivative pML2 (pBR322 deleted for base pairs 1140 to 2490) and contains adenovirus type 5 sequences extending from base pair 1 to base pair 5788 except that it is deleted for adenovirus type 5 base pairs 357 to 3327. At the site of the Ad5 357/3327 deletion a transcriptional unit is inserted which is comprised of the adenovirus type 2 major late promoter, the adenovirus type 2 tripartite leader cDNA and the human p53 cDNA. It is a typical E1 replacement vector deleted for the Ads E1a and E1b genes but containing the Ad5 protein IX gene (for review of Adenovirus vectors see: Graham and Prevec (1992)). Ad2 DNA was obtained from Gibco BRL. Restriction endonucleases and T4 DNA ligase were obtained from New England Biolabs. *E. coli* DH5α competent cells were purchased from Gibco BRL and 293 cells were obtained from the American Type Culture Collection (ATCC). Prep- A-Gene DNA purification resin was obtained from BioRad. LB broth bacterial growth medium was obtained from Difco. Qiagen DNA purification columns were obtained from Qiagen, Inc. Ad5 dl327 was obtained from R. J. Schneider, NYU. The MBS DNA transfection kit was purchased from Stratagene.

One (1) μg pAd/MLP/p53/E1b- was digested with 20 units each of restriction enzymes Ecl 136II and NgoMI according to the manufacturer's recommendations. Five (5) μg Ad2 DNA was digested with 20 units each of restriction endonucleases DraI and NgoMI according to the manufacturer's recommendations. The restriction digestions were loaded into separate lanes of a 0.8% agarose gel and electrophoresed at 100 volts for 2 hours. The 4268 bp restriction fragment from the Pad/MLP/p53/E1b- sample and the 6437 bp fragment from the Ad2 sample were isolated from the gel using Prep-A-Gene DNA extraction resin according to the manufacturer's specifications. The restriction fragments were mixed and treated with T4 DNA ligase in a total volume of 50 μl at 16° C. for 16 hours according to the manufacturer's recommendations. Following ligation 5 μl of the reaction was used to transform *E. coli* DH5α cells to ampicillin resistance following the manufacturer's procedure. Six bacterial colonies resulting from this procedure were used to inoculate separate 2 ml cultures of LB growth medium and incubated overnight at 37° C. with shaking. DNA was prepared from each bacterial culture using standard procedures (Sambrook et al. (1989)). One fourth of the plasmid DNA from each isolate was digested with 20 units of restriction endonuclease XhoI to screen for the correct recombinant containing XhoI restriction fragments of 3627, 3167, 2466 and 1445 base pairs. Five of six screened isolates contained the correct plasmid. One of these was then used to inoculate a 1 liter culture of LB medium for isolation of large quantities of plasmid DNA. Following overnight incubation plasmid DNA was isolated from the 1 liter culture using Qiagen DNA purification columns according to the manufacturer's recommendations. The resulting plasmid was designated Pad/MLP/p53/PIX-. Samples of this plasmid were deposited with the American Type Culture Collection, 12301 Parklawn Drive, Rockville, Md., U.S.A., 12301, on Oct. 22, 1993. The deposit was made under the provisions of the Budapest Treaty on the International Deposit of Microorganisms for the Purpose of Patent Procedure. The deposit was accorded ATCC Accession No. 75576.

To construct a recombinant adenovirus, 10 μg Pad/MLP/p53/PIX- were treated with 40 units of restriction endonuclease EcoRI to linearize the plasmid. Adenovirus type 5 dl327 DNA (Thimmappaya (1982)) was digested with restriction endonuclease ClaI and the large fragment (approximately 33 kilobase pairs) was purified by sucrose gradient centrifugation. Ten (10) μg of EcoRI treated Pad/MLP/p53/E1b- and 2.5 μg of ClaI treated Ad5 dl327 were mixed and used to transfect approximately $10^6$ 293 cells using the MBS mammalian transfection kit as recommended by the supplier. Eight (8) days following the transfection the 293 cells were split 1 to 3 into fresh media and two days following this adenovirus induced cytopathic effect became evident on the transfected cells. At 13 days post-transfection DNA was prepared from the infected cells using standard procedures (Graham and Prevec (1991)) and analyzed by restriction digestion with restriction endonuclease XhoI. Virus directed expression of p53 was verified following infection of SaoS2 osteosarcoma cells with viral lysate and immunoblotting with an anti-p53 monoclonal antibody designated 1801 (Novocasta Lab. Ltd., U.K.).

EXPERIMENT NO. II

Materials and Methods

Cell Lines

Recombinant adenoviruses were grown and propagated in the human embryonal kidney cell line 293 (ATCC CRL 1573) maintained in DME medium containing 10% defined, supplemented calf serum (Hyclone). Saos-2 cells were maintained in Kaighn's media supplemented with 15% fetal calf serum. HeLa and Hep 3B cells were maintained in DME medium supplemented with 10% fetal calf serum. All other cell lines were grown in Kaighn's media supplemented with 10% fetal calf serum. Saos-2 cells were kindly provided by Dr. Eric Stanbridge. All other cell lines were obtained from ATCC.

Construction of Recombinant Adenoviruses

To construct the Ad5/p53 viruses, a 1.4 kb HindIII-SmaI fragment containing the full length cDNA for p53 (Table 1 (SEQ ID NO: 9) was isolated from pGEM1-p53-B-T (kindly supplied by Dr. Wen Hwa Lee) and inserted into the multiple cloning site of the expression vector pSP72 (Promega) using standard cloning procedures (Sambrook et al. (1989)). The p53 insert was recovered from this vector following digestion with XhoI-BglII and gel electrophoresis. The p53 coding sequence was then inserted into either pNL3C or pNL3CMV adenovirus gene transfer vectors (kindly provided by Dr. Robert Schneider) which contain the Ad5 5' inverted terminal repeat and viral packaging signals and the E1a enhancer upstream of either the Ad2 major late promoter (MLP) or the human cytomegalovirus immediate early gene promoter (CMV), followed by the tripartite leader CDNA and Ad 5 sequence 3325–5525 bp in a PML2 background. These new constructs replace the E1 region (bp 360–3325) of Ad5 with p53 driven by either the Ad2 MLP (A/M/53) or the human CMV promoter (A/C/53), both followed by the tripartite leader CDNA (see FIG. 4). The p53 inserts use the remaining downstream E1b polyadenylation site. Additional MLP and CMV driven p53 recombinants (A/M/N/53, A/C/N/53) were generated which had a further 705 nucleotide deletion of Ad 5 sequence to remove the protein IX (PIX) coding region. As a control, a recombinant adenovirus was generated from the parental PNL3C plasmid without a p53 insert (A/M). A second control consisted of a recombinant adenovirus encoding the beta-galactosidase gene under the control of the CMV promoter (A/C/β-gal). The plasmids were linearized with either Nru I or Eco RI and co-transfected with the large fragment of a Cla I digested Ad 5 d1309 or d1327 mutants (Jones and Shenk (1979)) using a $Ca/PO_4$ transfection kit (Stratagene). Viral plaques were isolated and recombinants identified by both restriction digest analysis and PCR using recombinant specific primers against the tripartite leader CDNA sequence with downstream p53 CDNA sequence. Recombinant virus was further purified by limiting dilution, and virus particles were purified and titered by standard methods (Graham and van der Erb (1973); Graham and Prevec (1991)).

p53 Protein Detection

Saos-2 or Hep 3B cells ($5\times10^5$) were infected with the indicated recombinant adenoviruses for a period of 24 hours at increasing multiplicities of infection (MOI) of plaque forming units of virus/cell. Cells were then washed once with PBS and harvested in lysis buffer (50 mM Tris-HCl Ph 7.5, 250 Mm NaCl, 0.1% NP40, 50 mM NaF, 5 mM EDTA, 10μg/ml aprotinin, 10 ug/ml leupeptin, and 1 mM PMSF). Cellular proteins (approximately 30 μg) were separated by 10% SDS-PAGE and transferred to nitrocellulose. Membranes were incubated with α-p53 antibody PAb 1801 (Novocastro) followed by sheep anti-mouse IgG conjugated with horseradish peroxidase. p53 protein was visualized by chemiluminescence (ECL kit, Amersham) on Kodak XAR-5 film.

Measurement of DNA Synthesis Rate

Cells ($5\times10^3$/well) were plated in 96-well titer plates (Costar) and allowed to attach overnight (37° C., 7% $CO_2$). Cells were then infected for 24 hours with purified recombinant virus particles at MOIs ranging from 0.3 to 100 as indicated. Media were changed 24 hours after infection, and incubation was continued for a total of 72 hours. $^3$H-thymidine (Amersham, 1μCi/well) was added 18 hours prior to harvest. Cells were harvested on glass fiber filters and levels of incorporated radioactivity were measured in a beta scintillation counter. $^3$H-thymidine incorporation was expressed as the mean k (+/−SD) of media control and plotted versus the MOI.

Tumorigenicity in Nude Mice

Approximately $2.4\times10^8$ Saos-2 cells, plated in T225 flasks, were treated with suspension buffer (1% sucrose in PBS) containing either A/M/N/53 or A/M purified virus at an MOI of 3 or 30. Following an overnight infection, cells were injected subcutaneously into the left and right flanks of BALB/c athymic nude mice (4 mice per group). One flank was injected with the A/M/N/53 treated cells, while the contralateral flank was injected with the control A/M treated cells, each mouse serving as its own control. Animals receiving bilateral injection of buffer treated cells served as additional controls. Tumor dimensions (length, width and height) and body weights were then measured twice per week over an 8 week period. Tumor volumes were estimated for each animal assuming a spherical geometry with radius equal to one-half the average of the measured tumor dimensions.

Intra-tumoral RNA Analysis

BALB/c athymic nude mice (approximately 5 weeks of age) were injected subcutaneously with $1\times10^7$ H69 small cell lung carcinoma (SCLC) cells in their right flanks. Tumors were allowed to progress for 32 days until they were approximately 25–50 $mm^3$. Mice received peritumoral injections of either A/C/53 or A/C/β-gal recombinant adenovirus ($2\times10^9$ plaque forming units (pfu)) into the subcutaneous space beneath the tumor mass. Tumors were excised from the animals 2 and 7 days post adenovirus treatment and rinsed with PBS. Tumor samples were homogenized, and total RNA was isolated using a TriReagent kit (Molecular Research Center, Inc.). PolyA RNA was isolated using the PolyATract mRNA Isolation System (Promega), and approximately 10 ng of sample was used for RT-PCR determination of recombinant p53 mRNA expression (Wang et al. (1989)). Primers were designed to amplify sequence between the adenovirus tripartite leader CDNA and the downstream p53 CDNA, ensuring that only recombinant, and not endogenous p53 would be amplified.

p53 Gene Therapy of Established Tumors in Nude Mice

Approximately $1\times10^7$ H69 (SCLC) tumor cells in 200 μl volumes were injected subcutaneously into female BALB/c athymic nude mice. Tumors were allowed to develop for 2 weeks, at which point animals were randomized by tumor size (N=5/group). Peritumoral injections of either A/M/N/53 or the control A/M adenovirus ($2\times10^9$ pfu/injection) or buffer alone (1% sucrose in PBS) were administered twice per week for a total of 8 doses/group. Tumor dimensions and body weights were measured twice per week for 7 weeks, and tumor volume was estimated as described previously. Animals were then followed to observe the effect of treatment on mouse survival.

Results

Construction of Recombinant p53-Adenovirus p53 adenoviruses were constructed by replacing a portion of the E1a and E1b region of adenovirus Type 5 with p53 CDNA under the control of either the Ad2 MLP (A/M/53) or CMV (A/C/53) promoter (schematized in FIG. 4). This E1 substitution severely impairs the ability of the recombinant adenoviruses to replicate, restricting their propagation to 293 cells which supply Ad 5 E1 gene products in trans (Graham et al. (1977)). After identification of p53 recombinant adenovirus by both restriction digest and PCR analysis, the entire p53 CDNA sequence from one of the recombinant adenoviruses (A/M/53) was sequenced to verify that it was free of mutations. Following this, purified preparations of the p53 recombinants were used to infect HeLa cells to assay for the presence of phenotypically wild type adenovirus. HeLa cells, which are non-permissive for replication of E1-deleted adenovirus, were infected with $1–4\times10^9$ infectious units of recombinant adenovirus, cultured for 3 weeks, and observed for the appearance of cytopathic effect (CPE). Using this assay, recombinant adenovirus replication or wild type contamination was not detected, readily evident by the CPE observed in control cells infected with wild type adenovirus at a level of sensitivity of approximately 1 in $10^9$.

p53 Protein Expression from Recombinant Adenovirus

To determine if p53 recombinant adenoviruses expressed p53 protein, tumor cell lines which do not express endogenous p53 protein were infected. The human tumor cell lines Saos-2 (osteosarcoma) and Hep 3B (hepatocellular carcinoma) were infected for 24 hours with the p53 recombinant adenoviruses A/M/53 or A/C/53 at MOIs ranging 0.1 to 200 pfu/cell. Western analysis of lysates prepared from infected cells demonstrated a dose-dependent p53 protein expression in both cell types. Both cell lines expressed higher levels of p53protein following infection with A/C/53 than with A/M/53; (SEQ ID NO: 7–8). No p53 protein was detected in non-infected cells. Levels of endogenous wild-type p53 are normally quite low, and nearly undetectable by Western analysis of cell extracts (Bartek et al. (1991)). It is clear however that wild-type p53 protein levels are easily detectable after infection with either A/M/53 or A/C/53 at the lower MOIs, suggesting that even low doses of p53 recombinant adenoviruses can produce potentially efficacious levels of p53.

p53 Dependent Morphology Changes

The reintroduction of wild-type p53 into the p53-negative osteosarcoma cell line, Saos-2, results in a characteristic enlargement and flattening of these normally spindle-shaped cells (Chen et al. (1990)). Subconfluent Saos-2 cells ($1\times10^5$ cells/10 cm plate) were infected at an MOI of 50 with either the A/C/53 or control A/M virus, and incubated at 37° C. for 72 hours until uninfected control plates were confluent. At this point, the expected morphological change was evident in the A/C/53 treated plate but not in uninfected or control virus-infected plates. This effect was not a function of cell density because a control plate initially seeded at lower density retained normal morphology at 72 hours when its confluence approximated that of the A/C/53 treated plate. Previous results had demonstrated a high level of p53 protein expression at an MOI of 50 in Saos-2 cells, and these results provided evidence that the p53 protein expressed by these recombinant adenoviruses was biologically active.

p53 Inhibition of Cellular DNA Synthesis

To further test the activity of the p53 recombinant adenoviruses, their ability to inhibit proliferation of human tumor cells was assayed as measured by the uptake of $^3$H-thymidine. It has previously been shown that introduction of wild-type p53 into cells which do not express endogenous wild-type p53 can arrest the cells at the $G_1$/S transition, leading to inhibition of uptake of labeled thymidine into newly synthesized DNA (Baker et al. (1990); Mercer et al. (1990); Diller et al. (1990)). A variety of p53-deficient tumor cell lines were infected with either A/M/N/53, A/C/N/53 or a non-p53 expressing control recombinant adenovirus (A/M). A strong, dose-dependent inhibition of DNA synthesis by both the A/M/N/53 and A/C/N/53 recombinants in 7 out of the 9 different tumor cell lines tested was observed. Both constructs were able to inhibit DNA synthesis in these human tumor cells, regardless of whether they expressed mutant p53 or failed to express p53 protein. It also was found that in this assay, the A/C/N/53 construct was consistently more potent than the A/M/N/53. In saos-2 (osteosarcoma) and MDA-MB468 (breast cancer) cells, nearly 100% inhibition of DNA synthesis was achieved with the A/C/N/53 construct at an MOI as low as 10. At doses where inhibition by the control adenovirus in only 10–30%, a 50–100% reduction in DNA synthesis using either p53 recombinant adenovirus was observed. In contrast, no significant p53-specific effect was observed with either construct as compared to control virus in HEP G2 cells (hepatocarcinoma cell line expressing endogenous wild-type p53, Bressac et al. (1990)), nor in the KS62 (p53 null) leukemic cell line.

Tumorigenicity in Nude Mice

Figure 6:
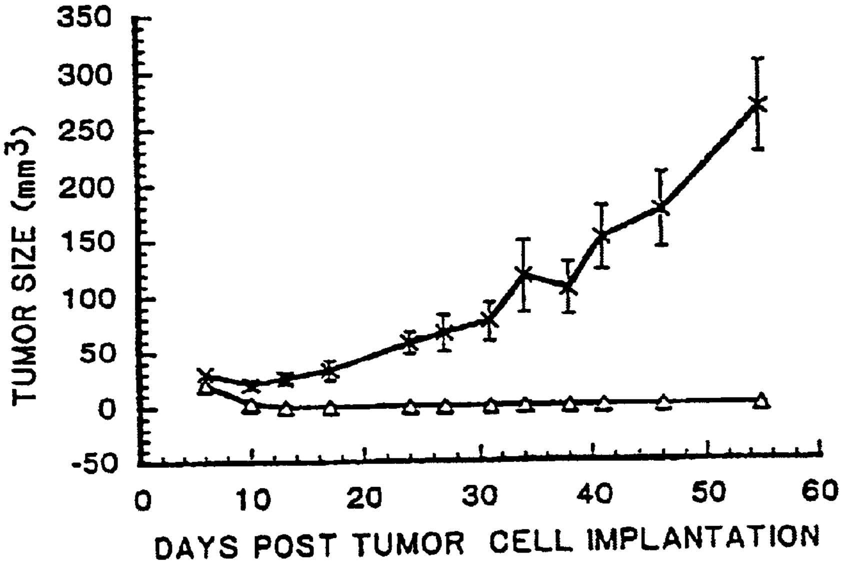
FIG. 6 shows tumorigenicity of p53 infected Saos-2 cells in nude mice. Saos-2 cells were infected with either the control A/M virus or the p53 recombinant A/M/N/53 at MOI=30. Treated cells were injected subcutaneously into the flanks of nude mice, and tumor dimensions were measured (as described in Experiment No. II) twice per week for 8 weeks. Results are plotted as tumor size versus days post tumor cell implantation for both control A/M (-x-x-) and A/M/N/53 (-Δ-Δ-) treated cells. Error bars represent the mean tumor size=/−SEM for each group of 4 animals at each time point.

In a more stringent test of function for the p53 recombinant adenoviruses, tumor cells were infected ex vivo and then injected the cells into nude mice to assess the ability of the recombinants to suppress tumor growth in vivo. Saos-2 cells infected with A/M/N/53 or control A/M virus at a MOI of 3 or 30, were injected into opposite flanks of nude mice. Tumor sizes were then measured twice a week over an 8 week period. At the MOI of 30, no tumor growth was observed in the p53-treated flanks in any of the animals, while the control treated tumors continued to grow (FIG. 6). The progressive enlargement of the control virus treated tumors were similar to that observed in the buffer treated control animals. A clear difference in tumor growth between the control adenovirus and the p53 recombinant at the MOI of 3, although tumors from 2 out of the 4 p53-treated mice did start to show some growth after approximately 6 weeks. Thus, the A/M/N/53 recombinant adenovirus is able to mediate p53-specific tumor suppression in an in vivo environment.

In Vivo Expression of Ad/p53

Although ex vivo treatment of cancer cells and subsequent injection into animals provided a critical test of tumor suppression, a more clinically relevant experiment is to determine if injected p53 recombinant adenovirus could infect and express p53 in established tumors in vivo. To address this, H69 (SCLC, $p53^{null}$) cells were injected subcutaneously into nude mice, and tumors were allowed to develop for 32 days. At this time, a single injection of $2\times10^9$ pfu of either A/C/53 or A/C/β-gal adenovirus was injected into the peritumoral space surrounding the tumor. Tumors were then excised at either Day 2 or Day 7 following the adenovirus injection, and polyA RNA was isolated from each tumor. RT-PCR, using recombinant-p53 specific primers, was then used to detect p53 MRNA in the p53 treated tumors. RT-PCR was carried out using equal RNA concentrations and primers specific for recombinant p53 message. PCR amplification was for 30 cycles at 94° C. 1 mm., 55° C. 1.5 min., 72° C. 2 min., and a 10 min., 72° C. final extension period in an Omnigen thermalcycler (Hybaid). The PCR primers used were a 5' Tripartite Leader cDNA (5'-CGCCACCGAGGGACCTGAGCGAGTC-3', SEQ ID NO:1) and a 3' p53 primer (5'-TTCTGGGAGGGACAGAAGA-3', SEQ ID NO:2). No p53 signal was evident from the tumors excised from the β-gal treated animals. Amplification with actin primers served as a control for the RT-PCR reaction while a plasmid containing the recombinant-p53 sequence served as a positive control for the recombinant-p53 specific band. This experiment demonstrates that a p53 recombinant adenovirus can specifically direct expression of p53 mRNA within established tumors following a single injection into the peritumoral space. It also shows in vivo viral persistence for at least one week following infection with a p53 recombinant adenovirus.

In Vivo Efficacy

Figure 7A:
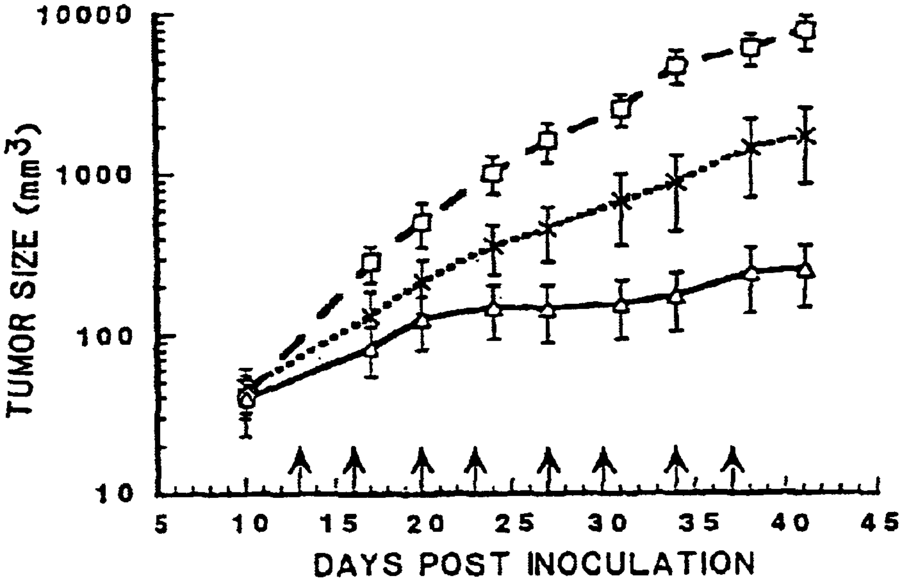
FIGS. 7A and 7B show in vivo tumor suppression and increased survival time with A/M/N/53. H69 (SCLC) tumor cells were injected subcutaneously into nude mice and allowed to develop for 2 weeks. Peritumoral injections of either buffer alone ( - - - ), control A/M adenovirus (-x-x-), or A/M/N/53 (-Δ-Δ), both viruses ($2\times10^9$ pfu/injection) were administered twice per week for a total of 8 doses. Tumor dimensions were measured twice per week and tumor volume was estimated as described in Experiment No. II. A) Tumor size is plotted for each virus versus time (days) post inoculation of H69 cells. Error bars indicate the mean tumor size+/−SEM for each group of 5 animals. Arrows indicate days virus injections. B) Mice were monitored for survival and the fraction of mice surviving per group versus time post inoculation of buffer alone ( - - - ), control A/M ( . . . . . . . . . ) or A/M/N/53 (–) virus treated H69 cells is plotted.
Figure 7B:
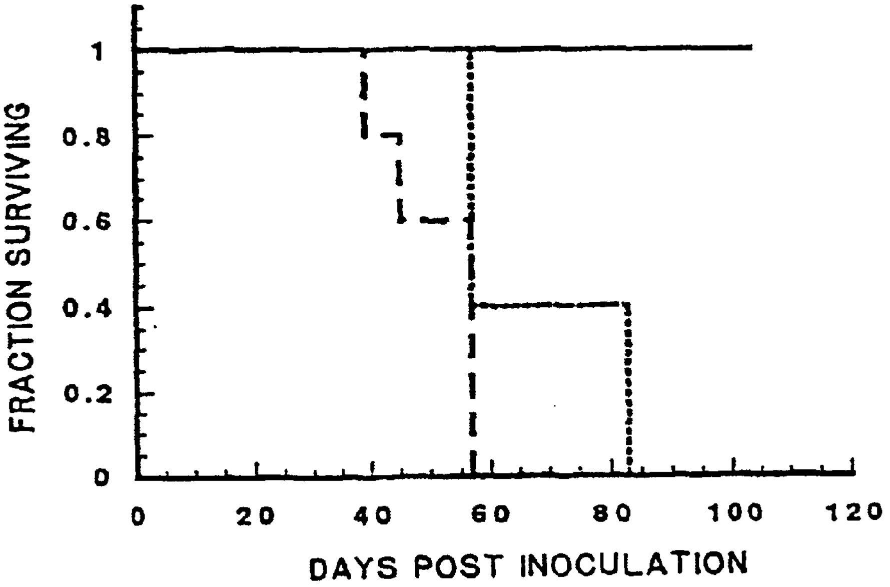

To address the feasibility of gene therapy of established tumors, a tumor-bearing nude mouse model was used. H69 cells were injected into the subcutaneous space on the right flank of mice, and tumors were allowed to grow for 2 weeks. Mice then received peritumoral injections of buffer or recombinant virus twice weekly for a total of 8 doses. In the mice treated with buffer or control A/M virus, tumors continued to grow rapidly throughout the treatment, whereas those treated with the A/M/N/53 virus grew at a greatly reduced rate (FIG. 7A). After cessation of injections, the control treated tumors continued to grow while the p53 treated tumors showed little or no growth for at least one week in the absence of any additional supply of exogenous p53 (FIG. 7A). Although control animals treated with buffer alone had accelerated tumor growth as compared to either virus treated group, no significant difference in body weight was found between the three groups during the treatment period. Tumor ulceration in some animals limited the relevance of tumor size measurements after day 42. However, continued monitoring of the animals to determine survival time demonstrated a survival advantage for the p53-treated animals (FIG. 7B). The last of the control adenovirus treated animals died on day 83, while buffer alone treated controls had all expired by day 56. In contrast, all 5 animals treated with the A/M/N/53 continue to survive (day 130 after cell inoculation) (FIG. 7B). Together, this data establish a p53-specific effect on both tumor growth and survival time in animals with established p53-deficient tumors.

Adenovirus Vectors Expressing p53

Recombinant human adenovirus vectors which are capable of expressing high levels of wild-type p53 protein in a dose dependent manner were constructed. Each vector contains deletions in the E1a and E1b regions which render the virus replication deficient (Challberg and Kelly (1979); Horowitz, (1991)). Of further significance is that these deletions include those sequences encoding the E1b 19 and 55 kd protein. The 19 kd protein is reported to be involved in inhibiting apoptosis (White et al. (1992); Rao et al. (1992)), whereas the 55 kd protein is able to bind wild-type p53 protein (Sarnow et al. (1982); Heuvel et al. (1990)). By deleting these adenoviral sequences, potential inhibitors of p53 function were removed through direct binding to p53 or potential inhibition of p53 mediated apoptosis. Additional constructs were made which have had the remaining 3' E1b sequence, including all protein IX coding sequence, deleted as well. Although this has been reported to reduce the packaging size capacity of adenovirus to approximately 3 kb less than wild-type virus (Ghosh-Choudhury et al. (1987)), these constructs are also deleted in the E3 region so that the A/M/N/53 and A/C/N/53 constructs are well within this size range. By deleting the pIX region, adenoviral sequences homologous to those contained in 293 cells are reduced to approximately 300 base pairs, decreasing the chances of regenerating replication-competent, wild-type adenovirus through recombination. Constructs lacking pIX coding sequence appear to have equal efficacy to those with pIX.

p53/Adenovirus Efficacy In Vitro

In concordance with a strong dose dependency for expression of p53 protein in infected cells, a dose-dependent, p53-specific inhibition of tumor cell growth was demonstrated. Cell division, was inhibited and demonstrated by the inhibition of DNA synthesis, in a wide variety of tumor cell types known to lack wild-type p53 protein expression. Bacchetti and Graham (1993) recently reported p53 specific inhibition of DNA synthesis in the ovarian carcinoma cell line SKOV-3 by a p53 recombinant adenovirus in similar experiments. In addition to ovarian carcinoma, additional human tumor cell lines were demonstrated, representative of clinically important human cancers and including lines over-expressing mutant p53 protein, can also be growth inhibited by the p53 recombinants of this invention. At MOIs where the A/C/N/53 recombinant is 90–100% effective in inhibiting DNA synthesis in these tumor types, control adenovirus mediated suppression is less than 20%.

Although Feinstein et al. (1992) reported that re-introduction of wild-type p53 could induce differentiation and increase the proportion of cells in G, versus $S+G_2$ for leukemic K562 cells, no p53 specific effect was found in this line. Horvath and Weber (1988) have reported that human peripheral blood lymphocytes are highly nonpermissive to adenovirus infection. In separate experiments, the recombinant significantly infected the non-responding K562 cells with recombinant A/C/β-gal adenovirus, while other cell lines, including the control Hep G2 line and those showing a strong p53 effect, were readily infectable. Thus, at least part of the variability of efficacy would appear to be due to variability of infection, although other factors may be involved as well.

Figure 8A:
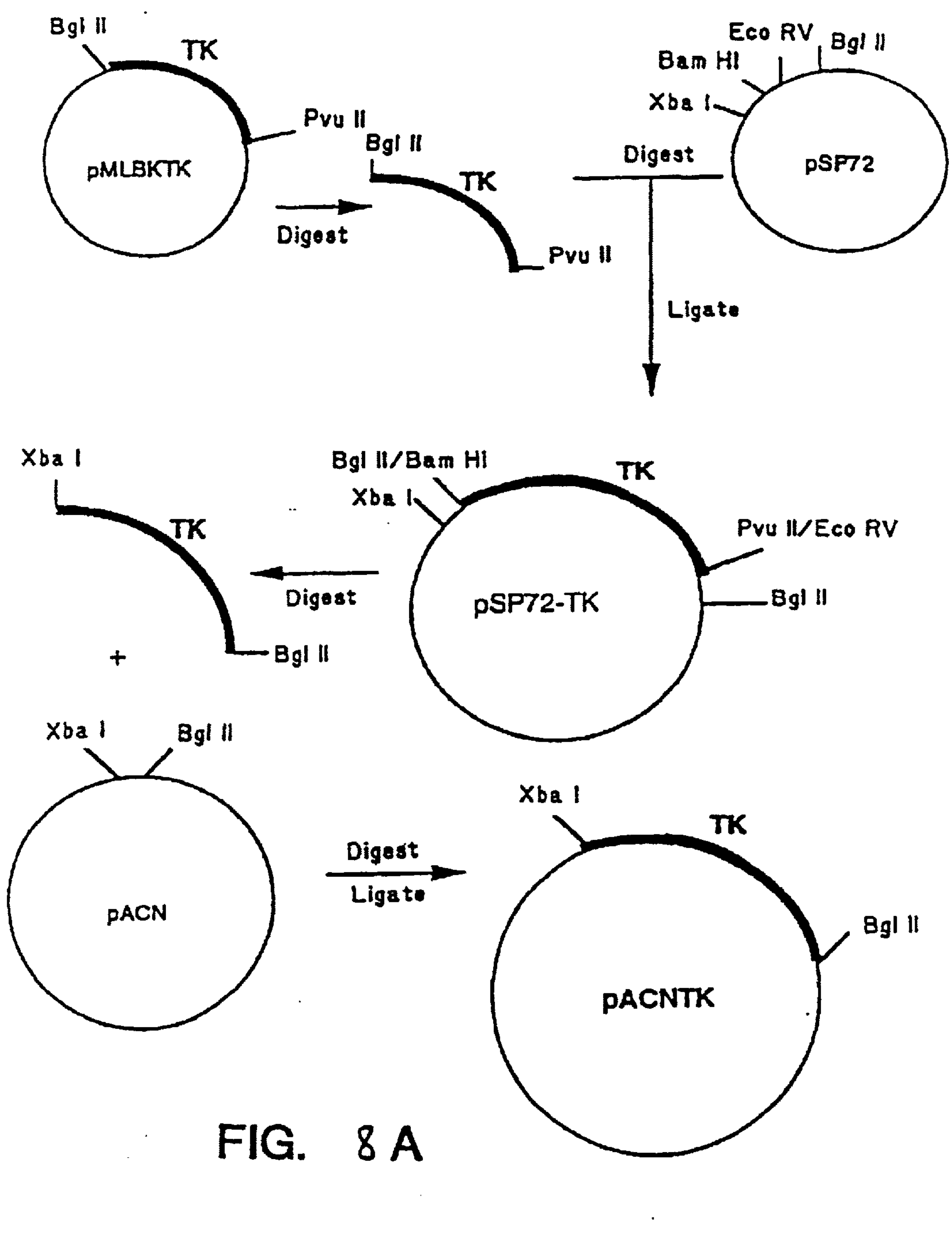
FIGS. 8A through 8C show maps of recombinant plasmid constructions. Plasmids were constructed as detailed in below. Bold lines in the constructs indicate genes of interest while boldface type indicates the restriction sites used to generate the fragments to be ligated together to form the subsequent plasmid as indicated by the arrows.
Figure 8:
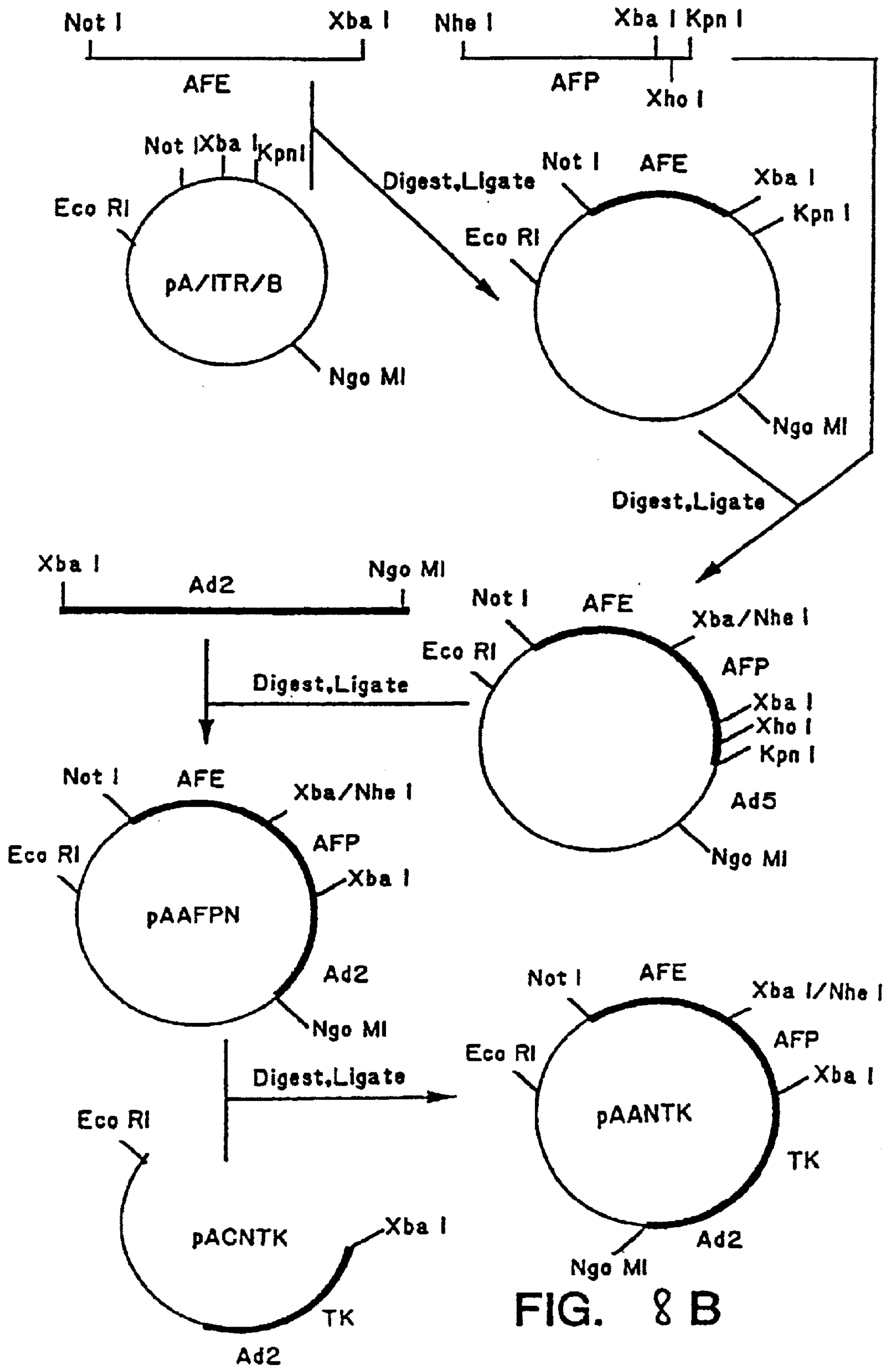
Figure 8C:
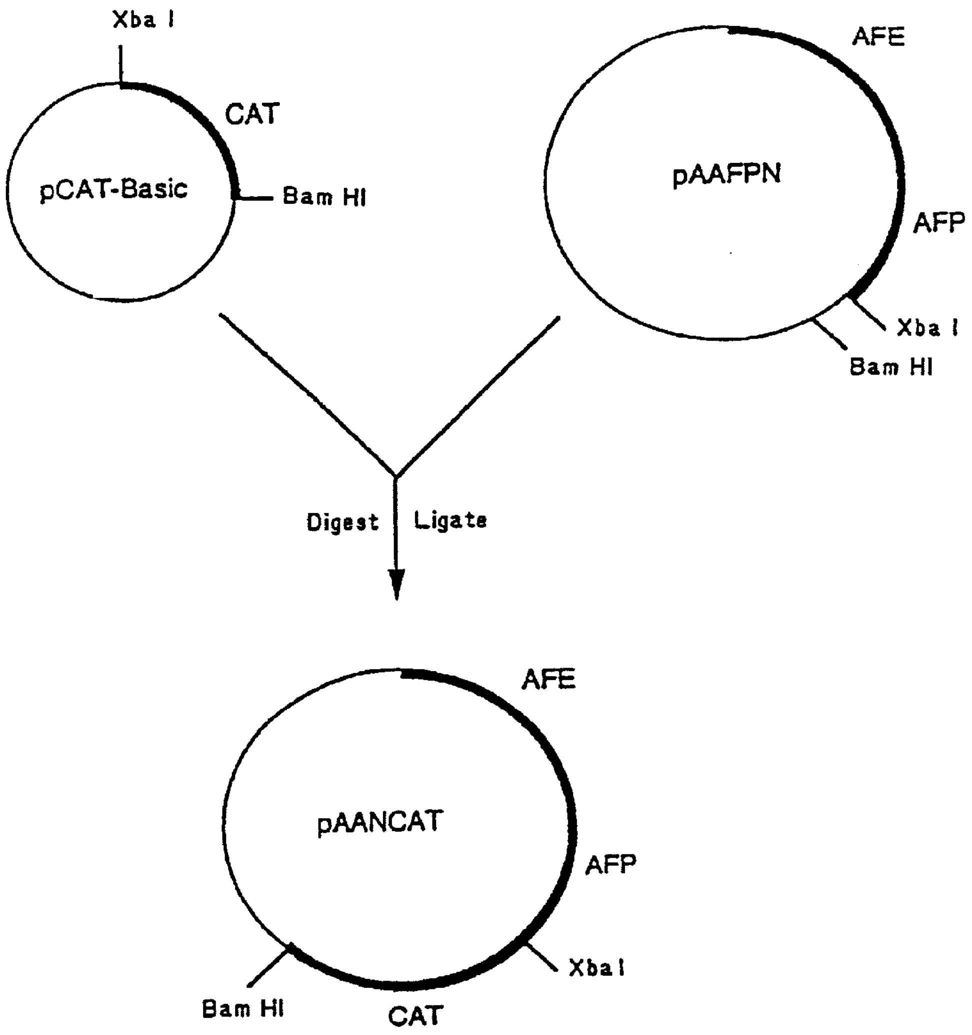

The results observed with the A/M/N/53 virus in FIG. 8 demonstrates that complete suppression is possible in an in vivo environment. The resumption of tumor growth in 2 out of 4, p53 treated animals at the lower MOI most likely resulted from a small percentage of cells not initially infected with the p53 recombinant at this dose. The complete suppression seen with A/M/N/53 at the higher dose, however, shows that the ability of tumor growth to recover can be overcome.

p53/Adenovirus In Vivo Efficacy

Figure 10A:
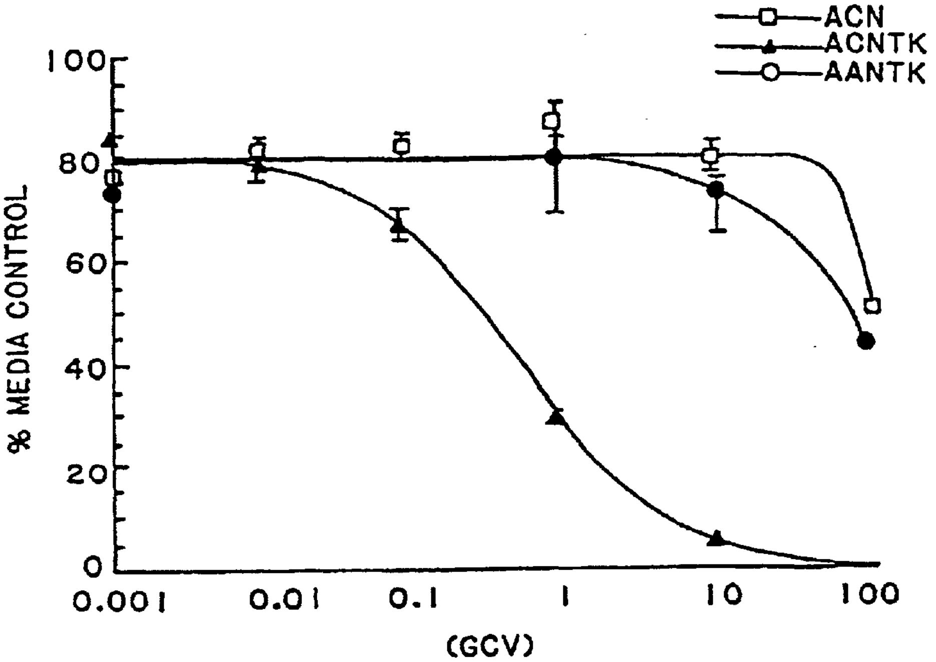
FIGS. 10A and 10B show the effects of TK/GCV treatment on two hepatocellular carcinoma cell lines and the effects of promoter specificity. Hep-G2 (AFP positive) and HLF (AFP negative) cell lines were infected overnight with ACNTK [-Δ-] AANTK [-▲-], or control ACN [-□-] virus at an infection multiplicity of 30 and subsequently treated with a single dose of ganciclovir at the indicated concentrations. Cell proliferation was assessed by adding $^3$H-thymidine to the cells approximately 18 hours prior to harvest. $^3$H-thymidine incorporation into cellular nucleic acid was measured 72 hours after infection (Top Count, Packard and expressed as a percent (mean+/−S.D.) of untreated control. The results show a non-selective dose dependent inhibition of proliferation with the CMV driven construct, while AFP driven TK selectively inhibits Hep-G2.
Figure 10B:
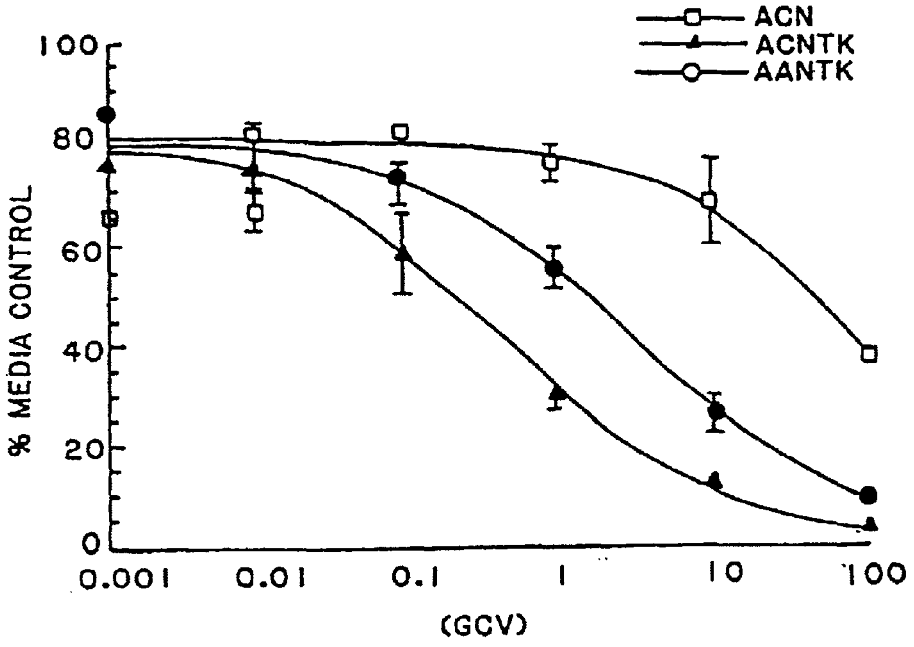
Figure 11:
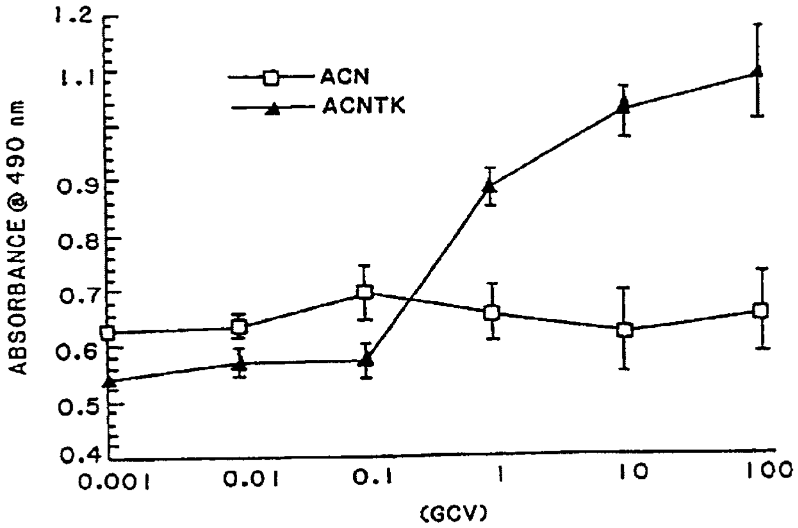
FIG. 11 shows cytotoxicity of ACNTK plus ganciclovir in HCC. HLF cells were infected at an MOI of 30 with either ACNTK [-●-] or the control virus ACN [-□-] and treated with ganciclovir at the indicated doses. Seventy-two (72) hours after ganciclovir treatment, the amount of lactate dehydrogenase (LDH) released into the cell supernatant were measured calorimetrically and plotted (mean+/−SEM) versus ganciclovir concentration for the two virus treated groups.

Work presented here and by other groups (Chen et al. (1990); Takahashi et al. (1992)) have shown that human tumor cells lacking expression of wild-type p53 can be treated ex vivo with p53 and result in suppression of tumor growth when the treated cells are transferred into an animal model. Applicants present the first evidence of tumor suppressor gene therapy of an in vivo established tumor, resulting in both suppression of tumor growth and increased survival time. In Applicants' system, delivery to tumor cells did not rely on direct injection into the tumor mass. Rather, p53 recombinant adenovirus was injected into the peritumoral space, and p53 mRNA expression was detected within the tumor. p53 expressed by the recombinants was functional and strongly suppressed tumor growth as compared to that of control, non-p53 expressing adenovirus treated tumors. However, both p53 and control virus treated tumor groups showed tumor suppression as compared to buffer treated controls. It has been demonstrated that local expression of tumor necrosis factor (TNF), interferon-γ), interleukin (IL)-2, IL-4 or IL-7 can lead to T-cell independent transient tumor suppression in nude mice (Hoch et al. (1992)). Exposure of monocytes to adenovirus virions are also weak inducers of IFN-α/β (reviewed in Gooding and Wold (1990)). Therefore, it is not surprising that some tumor suppression in nude mice was observed even with the control adenovirus. This virus mediated tumor suppression was not observed in the ex vivo control virus treated Saos-2 tumor cells described earlier. The p53-specific in vivo tumor suppression was dramatically demonstrated by continued monitoring of the animals in FIG. 10. The survival time of the p53-treated mice was significantly increased, with 5 out of 5 animals still alive more than 130 days after cell inoculation compared to 0 out of 5 adenovirus control treated animals. The surviving animals still exhibit growing tumors which may reflect cells not initially infected with the p53 recombinant adenovirus. Higher or more frequent dosing schedules may address this. In addition, promoter shutoff (Palmer et al. (1991)) or additional mutations may have rendered these cells resistant to the p53 recombinant adenovirus treatment. For example, mutations in the recently described WAF1 gene, a gene induced by wild-type p53 which subsequently inhibits progression of the cell cycle into S phase, (El-Deiry et al. (1993); Hunter (1993)) could result in a p53-resistant tumor.

EXPERIMENT NO. III

This Example shows the use of suicide genes and tissue specific expression of such genes in the gene therapy methods described herein. Hepatocellularcarcinoma was chosen as the target because it is one of the most common human malignancies affecting man, causing an estimated 1,250,000 deaths per year world-wide. The incidence of this cancer is very high in Southeast Asia and Africa where it is associated with Hepatitis B and C infection and exposure to aflatoxin. Surgery is currently the only treatment which offers the potential for curing HCC, although less than 20% of patients are considered candidates for resection (Ravoet C. et al., 1993). However, tumors other than hepatocellular carcinoma are equally applicable to the methods of reducing their proliferation described herein.

Cell Lines

All cell lines but for the HLF cell line were obtained from the American Type Tissue Culture Collection (ATCC) 12301 Parklawn Drive, Rockville Md. ATCC accession numbers are noted in parenthesis. The human embryonal kidney cell line 293 (CRL 1573) was used to generate and propagate the recombinant adenoviruses described herein. They were maintained in DME medium containing 10% defined, supplemented calf serum (Hyclone). The hepatocellular carcinoma cell lines Hep 3B (HB 8064), Hep G2 (HB 8065), and HLF were maintained in DME/F12 medium supplemented with 10% fetal bovine serum, as were the breast carcinoma cell lines MDA-MB468 (HTB 132) and BT-549 (HTB 122). Chang liver cells (CCL 13) were grown in MEM medium supplemented with 10% fetal bovine serum. The HLF cell line was obtained from Drs. T. Morsaki and H. Kitsuki at the Kyushu University School of Medicine in Japan.

RECOMBINANT VIRUS CONSTRUCTION

Figure 9:
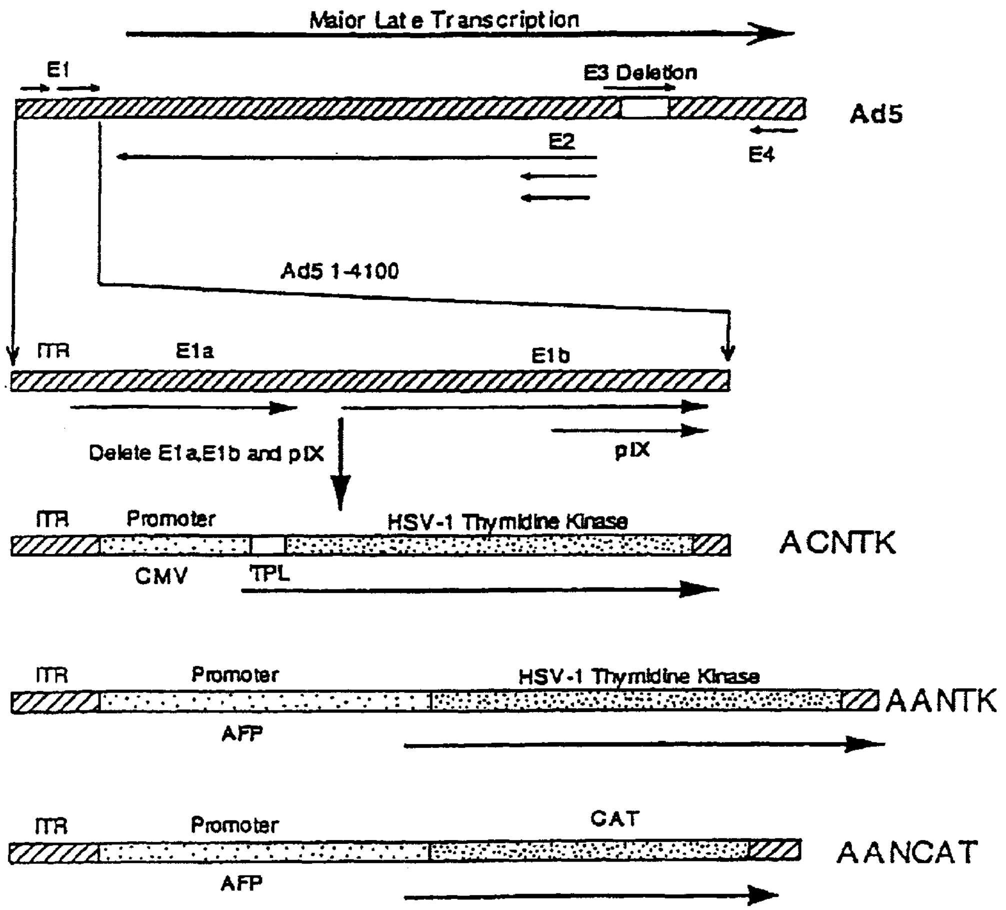
FIG. 9 is a schematic map of recombinant adenoviruses ACNTK, AANTK and AANCAT. To construct recombinant adenoviruses from the plasmids described in FIG. 11, 4 parts (20 μg) of either plasmid pACNTK, pAANTK, or pAANCAT were linearized with Eco R1 and cotransfected with 1 part (5 μg) of the large fragment of Cla 1 digested recombinant adenovirus (rACβ-gal) containing an E3 region deletion (Wills et al., 1994). In the resulting viruses, the Ad 5 nucleotides 360–4021 are replaced by either the CMV promoter and tripartite leader cDNA (TPL) or the α-fetoprotein enhancer and promoter (AFP) driving expression of the HSV-1 TK or CAT gene as indicated. The resulting recombinant adenoviruses are designated ACNTK, AANTK, and AANCAT respectively.

Two adenoviral expression vectors designated herein as ACNTK and AANTK and devoid of protein IX function (depicted in FIG. 8) are capable of directing expression of the TK suicide gene within tumor cells. A third adenovirus expression vector designated AANCAT was constructed to further demonstrate the feasibility of specifically targeting gene expression to specific cell types using adenoviral vectors. These adenoviral constructs were assembled as depicted in FIGS. 8 and 9 and are derivatives of those previously described for the expression of tumor suppresor genes.

For expression of the foreign gene, expression cassettes have been inserted that utilize either the human cytomegalovirus immediate early promoter/enhancer (CMV) (Boshart, M. et al., 1985) or the human alpha-fetoprotein (AFP) enhancer/promoter (Watanable, K. et al., 1987; Nakabayashi, H. et al., 1989) to direct transcription of the TK gene or the chloramphenicol acetyltransferase gene (CAT). The CMV enhancer promoter is capable of directing robust gene expression in a wide variety of cell types while the AFP enhancer/promoter construct restricts expression to hepatocellular carcinoma cells (HCC) which express AFP in about 70–80% of the HCC pateint population. In the construct utilizing the CMV promoter/enhancer, the adenovirus type 2 tripartite leader sequence also was inserted to enhance translation of the TK transcript (Berkner, K. L. and Sharp, 1985). In addition to the E1 deletion, both adenovirus vectors are additionally deleted for 1.9 kilobases (kb) of DNA in the viral E3 region. The DNA deleted in the E3 region is non-essential for virus propagation and its deletion increases the insert capacity of the recombinant virus for foreign DNA by an equivalent amount (1.9 kb) (Graham and Prevec, 1991).

To demonstrate the specificity of the AFP promoter/enhancer, the virus AANCAT also was constructed where the marker gene chloramphenicol aceyitransferase (CAT) is under the control of the AFP enhancer/promoter. In the ACNTK viral construct, the Ad2 tripartite leader sequence was placed between the CMV promoter/enhancer and the TK gene. The tripartite leader has been reported to enhance translation of linked genes. The E1 substitution impairs the ability of the recombinant viruses to replicate, restricting their propagation to 293 cells which supply the Ad5 E1 gene products in trans (Graham et al., 1977).

Adenoviral Vector ACNTK: The plasmid pMLBKTK in *E. coli* HB101 (from ATCC #39369) was used as the source of the herpes simplex virus (HSV-1) thymidine kinase (TK) gene. TK was excised from this plasmid as a 1.7 kb gene fragment by digestion with the restriction enzymes Bgl II and Pvu II and subcloned into the compatible Bam HI, EcoR V restriction sites of plasmid pSP72 (Promega) using standard cloning techniques (Sambrook et al., 1989). The TK insert was then isolated as a 1.7 kb fragment from this vector by digestion with Xba I and Bgl II and cloned into Xba I, BamHI digested plasmid pACN (Wills et al. 1994). Twenty (20) μg of this plasmid designated pACNTK were linearized with Eco RI and cotransfected into 293 cells (ATCC CRL 1573) with 5 μg of Cla I digested ACBGL (Wills et al., 1994 supra) using a $CaPO_4$ transfection kit (Stratagene, San Diego, California). Viral plaques were isolated and recombinants, designated ACNTK, were identified by restriction digest analysis of isolated DNA with Xho I and BsiWI. Positive recombinants were further purified by limiting dilution and expanded and titered by standard methods (Graham and Prevec, 1991).

Adenoviral Vector AANTK: The α-fetoprotein promoter (AFP-P) and enhancer (AFP-E) were cloned from a human genomic DNA (Clontech) using PCR amplification with primers containing restriction sites at their ends. The primers used to isolate the 210 bp AFP-E contained a Nhe I restriction site on the 5' primer and an Xba I, Xho I, Kpn I linker on the 3' primer. The 5' primer sequence was 5'-CGC GCT AGC TCT GCC CCA AAG AGC T-3 (SEQ ID NO: 3). The 5' primer sequence was 5'-CGC GGT ACC CTC GAG TCT AGA TAT TGC CAG TGG TGG AAG-3' (SEQ ID NO: 4). The primers used to isolate the 1763 bp AFE fragment contained a Not I restriction site on the 5' primer and a Xba I site on the 3' primer. The 5' primer sequence was 5'-CGT GCG GCC GCT GGA GGA CTT TGA GGA TGT CTG TC-3' (SEQ ID NO: 5). The 3' primer sequence was 5'-CGC TCT AGA GAG ACC AGT TAG GAA GTT TTC GCA-3' (SEQ ID NO: 6). For PCR amplification, the DNA was denatured at 97° for 7 minutes, followed by 5 cycles of amplification at 97°, 1 minute, 53°, 1 minute, 72°, 2 minutes, and a final 72°, 10 minute extension. The amplified AFE was digested with Not I and Xba I and inserted into the Not I, Xba I sites of a plasmid vector (pA/ITR/B) containing adenovirus type 5 sequences 1–350 and 3330–5790 separated by a polylinker containing Not I, Xho I, Xba I, Hind III, Kpn I, Bam HI, Nco I, Sma I, and Bgl II sites. The amplified AFP-E was digested with Nhe I and Kpn I and inserted into the AFP-E containing construct described above which had been digested with Xba I and Kpn I. This new construct was then further digested with Xba I and NgoMI to remove adenoviral sequences 3330–5780, which were subsequently replaced with an Xba I, NgoMI restriction fragment of plasmid pACN containing nucleotides 4021–10457 of adenovirus type 2 to construct the plasmid pAAN containing both the α-fetoprotein enhancer and promoter. This construct was then digested with Eco RI and Xba I to isolate a 2.3 kb fragment containing the Ad5 inverted terminal repeat, the AFP-E and the AFP-P which was subsequently ligated with the 8.55 kb fragment of Eco RI, Xba I digested pACNTK described above to generate pAANTK where the TK gene is driven by the α-fetoprotein enhancer and promoter in an adenovirus background. This plasmid was then linearized with Eco RI and cotransfected with the large fragment of Cla I digested ALBGL as above and recombinants, designated AANTK, were isolated and purified as described above.

Adenoviral Vector AANCAT: The chloramphenicol acetyltransferase (CAT) gene was isolated from the pCAT-Basic Vector (Promega Corporation) by an Xba I, Bam HI digest. This 1.64 kb fragment was ligated into Xba I, Bam HI digested pAAN (described above) to create pAANCAT. This plasmid was then linearized with Eco RI and cotransfected with the large fragment of Cla I digested rA/C/β-gal to create AANCAT.

Reporter Gene Expression: β-Galactosidase Expression:

Cells were plated at $1\times10^5$ cells/well in a 24-well tissue culture plate (Costar) and allowed to adhere overnight (37C, 7% $CO_2$). Overnight infections of ACBGL were performed at a multiplicity of infection (MOI) of 30. After 24 hours, cells were fixed with 3.7% Formaldehyde; PBS, and stained with 1 mg/ml Xgal reagent (USB). The data was scored (+,++,+++) by estimating the percentage of positively stained cells at each MOI. [+=1–33%, ++=33–67% and +++=>67%]

Reporter Gene Expression: Cat Expression:

Two $(2)\times10^6$ cells (Hep G2, Hep 3B, HLF, Chang, and MDA-MB468) were seeded onto 10 cm plates in triplicate and incubated overnight (37C, 7% $CO_2$). Each plate was then infected with either AANCAT at an MOI=30 or 100 or uninfected and allowed to incubate for 3 days. The cells were then trypsinized and washed with PBS and resuspended in 100 μl of 0.25 M Tris pH 7.8. The samples were frozen and thawed 3 times, and the supernatant was transferred to new tubes and incubated at 60° C. for 10 minutes. The samples were then spun at 4° C. for 5 minutes, and the supernatants assayed for protein concentration using a Bradford assay (Bio-Rad Protein Assay Kit). Samples were adjusted to equal protein concentrations to a final volume of 75 μl using 0.25 M Tris, 25 μl of 4 mM acetyl CoA and 1 μl of $^{14}C$-Chloramphenicol and incubated overnight at 37° C. 500 μl of ethyl acetate is added to each sample and mixed by vortexing, followed by centrifiguration for 5 minutes at room temperature. The upper phase is then transferred to a new tube and the ethyl acetate is evaporated by centrifugation under vacuum. The reaction products are then redissolved in 25 μl of ethyl acetate and spotted onto a thin layer chromatography (TLC) plate and the plate is then placed in a pre-equilibrated TLC chamber (95% chloroform, 5% methanol). The solvent is then allowed to migrate to the top of the plate, the plate is then dried and exposed to X-ray film.

Cellular Proliferation: $^3H$-Thymidine Incorporation

Cells were plated at $5\times10^3$ cells/well in a 96-well microtiter plate (Costar) and allowed to incubate overnight (37C, 7% $CO_2$). Serially diluted ACN, ACNTK or AATK virus in DMEM; 15% FBS; 1% glutamine was used to transfect cells at an infection multiplicity of 30 for an overnight duration at which point cells were dosed in triplicate with ganciclovir (Cytovene) at log intervals betweem 0.001 and 100 mM (micro molar). 1 μCi $^3H$-thymidine (Amersham) was added to each well 12–18 hours before harvesting. At 72 hours-post infection cells were harvested onto glass-fiber filters and incorporated $^3H$-thymidine was counted using liquid scintillation (TopCount, Packard). Results are plotted as percent of untreated control proliferation and tabulated as the effective dose ($ED_{50}\pm SD$) for a 50 percent reduction in proliferation over media controls. $ED_{50}$ values were estimated by fitting a logistic equation to the dose response data.

Cytotoxicity: LDH Release

Cells (HLF, human HCC) were plated, infected with ACN or ACNTK and treated with ganciclovir as described for the proliferation assay. At 72 hours post-ganciclovir administration, cells were spun, the supernatant was removed. The levels of lactate dehydrogenase measured colometrically (Promega, Cytotox 96™). Mean (+/−S.D.) LDH release is plotted versus M.O.I.

In Vivo Therapy

Human hepatocellular carcinoma cells (Hep 3B) were injected subcutaneously into ten female (10) athymic nu/nu mice (Simonsen Laboratories, Gilroy, Calif.). Each animal received approximately $1\times10^7$ cells in the left flank. Tumors were allowed to grow for 27 days before randomizing mice by tumor size. Mice were treated with intratumoral and peritumoral injections of ACNTK or the control virus ACN ($1\times10^9$ iu in 100 μl) every other day for a total of three doses. Starting 24 hours after the initial dose of adenovirus, the mice were dosed intraperitoneally with ganciclovir (Cytovene 100 mg/kg) daily for a total of 10 days. Mice were monitored for tumor size and body weight twice weekly. Measurements on tumors were made in three dimensions using vernier calipers and volumes were calculated using the formula $4/3\ \pi\ r^3$, where r is one-half the average tumor dimension.

Results

The recombinant adenoviruses were used to infect three HCC cell lines (HLF, Hep3B and Hep-G2). One human liver cell line (Chang) and two breast cancer cell lines were used as controls (MDAMB468 and BT549). To demonstrate the specificity of the AFP promoter/enhancer, the virus AANCAT was constructed. This virus was used to infect cells that either do (Hep 3B, HepG2) or do not (HLE, Chang, MDAMB468) express the HCC tumor marker alpha-fetoprotein (AFP). AANCAT directed expression of the CAT marker gene only in those HCC cells which are capable of expressing AFP.

The efficacy of ACNTK and AANTK for the treatment of HCC was assessed using a $^3H$-thymidine incorporation assay to measure the effect of the combination of HSV-TK expression and ganciclovir treatment upon cellular proliferation. The cell lines were infected with either ACNTK or AANTK or the control virus ACN (Wills et al., 1994 supra), which does not direct expression of HSV-TK, and then treated with increasing concentrations of ganciclovir. The effect of this treatment was assessed as a function of increasing concentrations of ganciclovir, and the concentration of ganciclovir required to inhibit $^3H$-thymidine incorporated by 50% was determined ($ED_{50}$). Additionally, a relative measure of adenovirus—mediated gene transfer and expression of each cell line was determined using a control virus which directs expression of the marker gene beta-galactosidase. The data presented in FIGS. 10A and 10B and Table 2 below show that the ACNTK virus/ganciclovir combination treatment was capable of inhibiting cellular proliferation in all cell lines examined as compared with the control adenovirus ACN in combination with ganciclovir. In contrast, the AANTK viral vector was only effective in those HCC cell lines which have been demonstrated to express α-fetoprotein. In addition, the AANTK/GCV combination was more effective when the cells were plated at high densities.

TABLE 2

| Cell Line | aFP | β-gal Expression | ACN | ED50 ACNTK | AANTK |
|---|---|---|---|---|---|
| MDAMB468 | − | +++ | >100 | 2 | >100 |
| BT549 | − | +++ | >100 | <0.3 | >100 |
| HLF | − | +++ | >100 | 0.8 | >100 |
| CHANG | − | +++ | >100 | 22 | >100 |
| HEP-3B | − | + | 80 | 8 | 8 |
| HEP-G2 LOW | + | ++ | 90 | 2 | 35 |
| HEP-G2 HIGH | + | ++ | 89 | 0.5 | 4 |

Figure 12A:
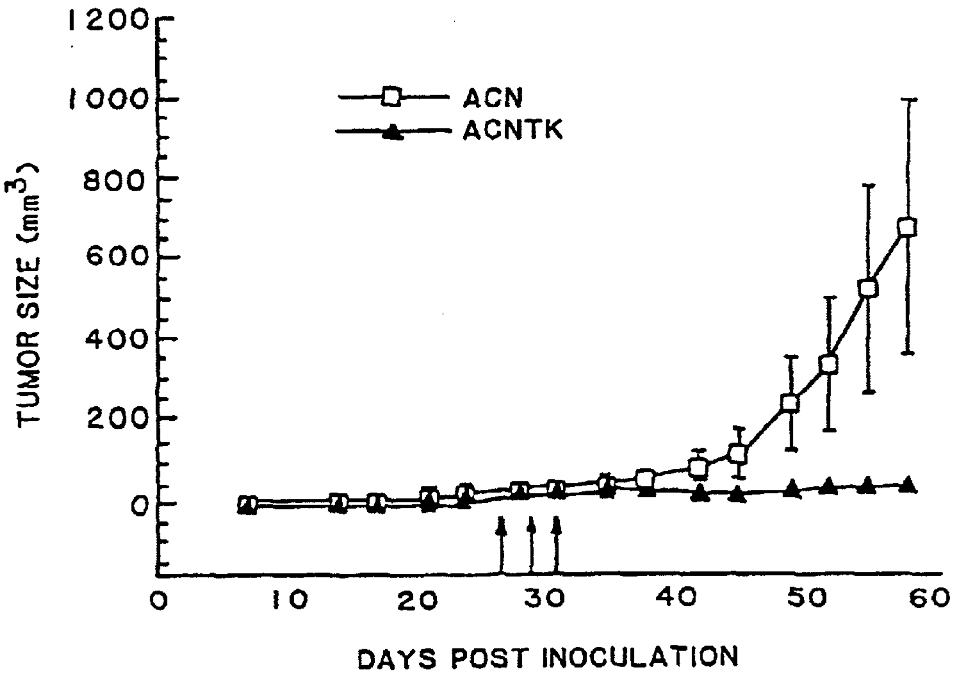
FIGS. 12A and 12B show the effect of ACNTK plus ganciclovir on established hepatocellular carcinoma (HCC) tumors in nude mice. One (1)×10$^7$ Hep 3B cells were injected subcutaneously into the flank of female nude mice and allowed to grow for 27 days. Mice then received intratumoral and peritumoral injections of either the ACNTK [-●-] or control ACN [-□-] virus (1×10$^9$ iu in 100 μl volume) every other day for a total of three doses (indicated by arrows). Injections of ganciclovir (100 mg/kg ip) began 24 hours after the initial virus dose and continued for a total of 10 days.
Figure 12B:
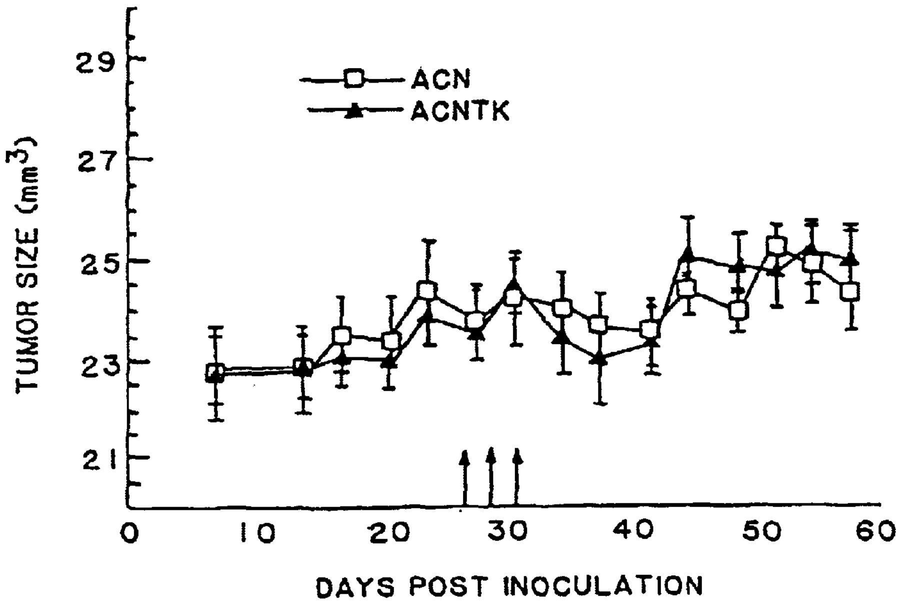

Nude mice bearing Hep3B tumors (N=5/group) were treated intratumorally and peritumorally with equivalent doses of ACNTK or ACN control. Twenty-four hours after the first administration of recombinant adenovirus, daily treatment of ganciclovir was initiated in all mice. Tumor dimensions from each animal were measured twice weekly via calipers, and average tumor sizes are plotted in FIGS. 12A and 12B. Average tumor size at day 58 was smaller in the ACNTK-treated animals but the difference did not reach statistical significance ($p<0.09$, unpaired t-test). These data support a specific effect of ACNTK on tumor growth in vivo. No significant differences in average body weight were detected between the groups.

Although the invention has been described with reference to the above embodiments, it should be understood that various modifications can be made without departing from the spirit of the invention. Accordingly, the invention is limited only by the claims that follow.

REFERENCES

AIELLO, L. et al. (1979) Virology 94:460–469.

AMERICAN CANCER SOCIETY. (1993) Cancer Facts and Figures.

AULITZKY et al. (1991) Eur. J. Cancer 27(4):462–467.

AUSTIN, E. A. and HUBER, B. E. (1993) Mol. Pharmaceutical 43:380–387.

BACCHETTI, S. AND GRAHAM, F. (1993) International Journal of Oncology 3:781–788.

BAKER S. J., MARKOWITZ, S., FEARON E. R., WILLSON, J. K. V., AND VOGELSTEIN, B. (1990) Science 249:912–915.

BARTEK, J., BARTKOVA, J., VOJTESEK, B., STASKOVA, Z., LUKAS, J., REJTHAR, A., KOVARIK,

J., MIDGLEY, C. A., GANNON, J. V., AND LANE, D. P. (1991) Oncogene 6:1699–1703.
BERKNER, K. L. and SHARP (1985) Nucleic Acids Res 13:841–857.
BOSHART, M. et al. (1985) Cell 41:521–530.
BRESSAC, B., GALVIN, K. M., LIANG, T. J., ISSELBACHER, K. J., WANDS, J. R., AND OZTURK, M. (1990) Proc. Natl. Acad. Sci. USA 87:1973–1977.
CARUSO M. et al. (1993) Proc. Natl. Acad. Sci. USA 90:7024–7028.
CHALLBERG, M. D., KELLY, T. J. (1979) Biochemistry 76:655–659.
CHEN P. L., CHEN Y., BOOKSTEIN R., AND LEE W. H. (1990) Science 250:1576–1580.
CHEN, Y., CHEN, P. L., ARNAIZ, N., GOODRICH, D., AND LEE, W. H. (1991) Oncogene 6:1799–1805.
CHENG, J L, YEE, J. K., YEARGIN, J., FRIEDMANN, T., AND HAAS, M. (1992) Cancer Research 52:222–226.
COLBY, W. W. AND SHENK, T. J. (1981) Virology 39:977–980.
CULVER ET AL. (1991) P.N.A.S. (U.S.A.) 88:3155–3159.
CULVER, K. W. et al. (1992) Science 256:1550–1552.
DEMETRI et al. (1989) J. Clin. Oncol. 7(10):1545–1553.
DILLER, L., et al. (1990) Mol. Cell. Biology 10: 5772–5781.
EL-DEIRY, W. S., et al. (1993) Cell 75:817–825.
EZZIDINE, Z. D. et al. (1991) The New Biologist 3:608–614.
FEINSTEIN, E., GALE, R. P., REED, J., AND CANAANI, E. (1992) Oncogene 7:1853–1857.
GHOSH-CHOUDHURY, G., HAJ-AHMAD, Y., AND GRAHAM, F. L. (1987) EMBO Journal 6:1733–1739.
GOODING, L. R., AND WOLD, W. S. M. (1990) Crit. Rev. Immunol. 10:53–71.
GRAHAM F. L., AND VAN DER ERB A. J. (1973) Virology 52:456–467.
GRAHAM, F. L. AND PREVEC, L. (1992) *Vaccines: New Arproaches to Immunological Problems*. R. W. Ellis (ed), Butterworth-Heinemann, Boston. pp. 363–390.
GRAHAM, F. L., SMILEY, J., RUSSELL, W. C. AND NAIRN, R. (1977) J. Gen. Virol. 36:59–74.
GRAHAM F. L. AND PREVEC L. (1991) Manipulation of adenovirus vectors. In: *Methods in Molecular Biolocy. Vol 7: Gene Transfer and Expression Protocols*. Murray E. J. (ed.) The Humana Press Inc., Clifton N.J., Vol 7:109–128.
HEUVEL, S. J. L., LAAR, T., KAST, W. M., MELIEF, C. J. M., ZANTEMA, A., AND VAN DER EB, A. J. (1990) EMBO Journal 9:2621–2629.
HOCK, H., DORSCH, M., KUZENDORF, U., QIN, Z., DIAMANTSTEIN, T., AND BLANKENSTEIN, T. (1992) Proc. Natl. Acad. Sci. USA 90:2774–2778.
HOLLSTEIN, M., SIDRANSKY, D., VOGELSTEIN, B., AND HARRIS, C. (1991) Science 253:49–53.
HOROWITZ, M. S. (1991) Adenoviridae and their replication. *In Fields Virology*. B. N. Fields, ed. (Raven Press, New York) pp. 1679–1721.
HORVATH, J., AND WEBER, J. M. (1988) J. Virol. 62:341–345.
HUANG et al. (1991) Nature 350:160–162.
HUBER, B. E. et al. (1991) Proc. Natl. Acad. Sci. USA 88:8039–8043.
HUNTER, T. (1993) Cell 75:839–841.
JONES, N. AND SHENK, T. (1979) Cell 17:683–689.
KAMB et al. (1994) Science 264:436–440.
KEURBITZ, S. J., PLUNKETT, B. S., WALSH, W. V., AND KASTAN, M. B. (1992) Proc. Natl. Acad. Sci. USA 89:7491–7495.
KREIGLER, M. *Gene Transfer and Expression: A Laboratory Manual*, W. H. Freeman and Company, New York (1990).
LANDMANN et al. (1992) J. Interferon Res. 12(2) :103–111.
LANE, D. P. (1992) Nature 358:15–16.
LANTZ et al. (1990) Cytokine 2(6):402–406.
LARRICK, J. W. and BURCK, K. L. *Gene Therapy: Application of Molecular Biology*, Elsevier Science Publishing Co., Inc. New York, N.Y. (1991).
LEE et al. (1987) Science 235:1394–1399.
LEMAISTRE et al. (1991) Lancet 337:1124–1125.
LEMARCHAND, P., et al. (1992) Proc. Natl. Acad. Sci. USA 89:6482–6486.
LEVINE, A. J. (1993) The Tumor Suppressor Genes. Annu. Rev. Biochem. 1993. 62:623–651.
LOWE S. W., SCHMITT, E. M., SMITH, S. W., OSBORNE, B. A., AND JACKS, J. (1993) Nature 362:847–852.
LOWE, S. W., RULEY, H. E., JACKS, T., AND HOUSMAN, D. E. (1993) Cell 74:957–967.
MARTIN (1975) In: *Remington's Pharm. Sci.*, 15th Ed. (Mack Publ. Co., Easton).
MERCER, W. E., et al. (1990) Proc. Natl. Acad. Sci. USA 87:6166–6170.
NAKABAYASHI, H. et al. (1989) The Journal of Biological Chemistry 264:266–271.
PALMER, T. D., ROSMAN, G. J., OSBORNE, W. R., AND MILLER, A. D. (1991) Proc. Natl. Acad Sci USA 88:1330–1334.
RAO, L., DEBBAS, M., SABBATINI, P., HOCKENBERY, D., KORSMEYER, S., AND WHITE, E. (1992) Proc. Natl. Acad. Sci. USA 89:7742–7746.
RAVOET C. et al. (1993) Journal of Surgical Oncology Supplement 3:104–111.
RICH, D. P., et al. (1993) Human Gene Therapy 4:460–476.
ROSENFELD, M. A., et al. (1992) Cell 68:143–155.
SAMBROOK J., FRITSCH E. F., AND MANIATIS T. (1989). *Molecular Cloning: A Laboratory Manual*. (Cold Spring Harbor Laboratory Press, Cold Spring Harbor).
SARNOW, P., HO, Y. S., WILLIAMS, J., AND LEVINE, A. J. (1982) Cell 28:387–394.
SHAW, P., BOVEY, R., TARDY, S., SAHLI, R., SORDAT, B., AND COSTA, J. (1992) Proc. Natl. Acad. Sci. USA 89:4495–4499.
SIEGFRIED, W. (1993) Exp. Clin. Endocrinol. 101:7–11.
SORSCHER, E. J. et al. (1994) Gene Therapy 1:233–238.
SPECTOR, D. J. (1983) Virology 130:533–538.
STEWART, P. L. et al. (1993) EMBO Journal 12:2589–2599.
STRAUS. S. E. (1984) Adenovirus infections in humans. In: *The Adenoviruses*, Ginsberg H S, ed. New York: Plenum Press, 451–496.
SUPERSAXO et al. (1988) Pharm. Res. 5(8):472–476.
TAKAHASHI, T., et al. (1989) Science 246: 491–494.
TAKAHASHI, T., et al. (1992) Cancer Research 52:2340–2343.
THIMMAPPAYA, B. et al. (1982) Cell 31:543–551.
WANG, A. M., DOYLE, M. V., AND MARK, D. F. (1989) Proc. Natl. Acad. Sci USA 86:9717–9721.
WATANABLE, K. et al. (1987) The Journal of Biological Chemistry 262:4812–4818.
WHITE, E., et al. (1992) Mol. Cell. Biol. 12:2570–2580.
WILLS, K. N. et al. (1994) Hum. Gen. Ther. 5:1079–1088.
YONISH-ROUACH, E., et al. (1991) Nature 352:345–347.

What is claimed is:

1. A method for obtaining expression of a tumor suppressor gene in a tumor cell in a mammal in vivo, wherein the tumor cell is caused by the absence of a tumor suppressor gene or the presence of a pathologically mutated tumor suppressor gene, the method comprising:

contacting the tumor cell with an effective amount of a replication-deficient recombinant adenovirus expression vector comprising: a) a partial or total deletion of a protein IX-encoding DNA sequence, and b) a gene encoding a foreign protein having a tumor suppressive function, wherein said contacting comprises intratumoral, peritumoral or intravesicular injection of the recombinant adenenovirus expression vector under suitable conditions such that the foreign protein is expressed in the tumor cell.

2. A method of inhibiting the proliferation of a tumor cell in a mammal, wherein the tumor cell is caused by the absence of a tumor suppressor gene or the presence of a pathologically mutated tumor suppressor gene, the method comprising:

administering to the mammal an effective amount of a replication-deficient recombinant adenovirus expression vector comprising: a) a partial or total deletion of a protein IX-encoding DNA sequence; and b) a gene encoding a foreign functional protein having a tumor suppressive function under suitable conditions to the mammal, wherein said administering comprises intratumoral, peritumoral or intravesicular injection of the replication-deficient recombinant adenenovirus vector under suitable conditions such that the foreign functional protein is expressed in the tumor cell.

3. The method of claim 1 or 2, wherein the tumor suppressor gene encodes a protein selected from the group p53, p21, p16, Rb, Wilm's tumor WT1 protein, h-NUC, mitosin and mito and p21.

4. The method of claim 1 or 2, wherein the tumor suppressor gene encodes p53.

5. The method of claim 1 or 2, wherein the gene is a suicide gene.

6. The method of claim 1 or 2, wherein the tumor cell is a member selected from the group consisting of non-small cell lung cancer, small cell lung cancer, hepatocarcinoma, melanoma, retinoblastoma, breast tumor, colorectal carcinoma, leukemia, lymphoma, brain tumor, cervical carcinoma, sarcoma, prostate tumor, bladder tumor, tumor of the reticuloendothelial tissues, Wilm's tumor, astrocytoma, glioblastoma, neuroblastoma, ovarian carcinoma, osteosarcoma, or renal cancer.

7. The method of claim 1 or 2, wherein deletion of the protein IX-encoding DNA sequence extends from about 3500 bp from the 5' viral termini to about 4000 bp from the 5' viral termmi.

8. The method of claim 1 or 2, wherein the recombinant adenovirus expression vector further comprises a deletion of a non-essential DNA sequence in adenovirus early region 3 or early region 4.

9. The method of claim 1 or 2, wherein the recombinant adenovirus expression vector further comprises a deletion of DNA sequences designated adenovirus E1a and E1b.

10. The method of claim 1 or 2, wherein the recombinant adenovirus expression vector further comprises a deletion of early region 3 or 4 and DNA sequences designated adenovirus E1a and E1b.

11. The method of claim 1 or 2, wherein the recombinant adenovirus expression vector is a Group C adenovirus selected from a serotype 1, 2, 5 or 6.

12. The method of claim 1 or 2, wherein the recombinant adenovirus expression vector is selected from the group consisting of A/C/N/53 and A/M/N/53.

13. The method of claim 1 or 2, further comprising administering a therapeutic agent that controls cell cycle progression and/or induces cell death.

14. The method of claim 1 or 2, wherein the mammal is a human.

15. The method of claim 10, wherein the recombinant adenovirus expression vector further comprises a deletion of up to forty nucleotides positioned 3' to the site of the adenovirus E1a and E1b DNA sequence deletions, and the site of the partial or total deletion of the protein IX-encoding sequence, and wherein said foreign functional protein comprises a polyadenlyation signal.

16. A method for obtaining expression of a suicide protein in a cell, the method comprising administering to the cell an effective amount of a recombinant adenovirus expression vector comprising: a) a partial or total deletion of a protein IX-eneoding DNA sequence, and b) a gene encoding a suicide protein, wherein an mRNA encoding the suicide protein is produced by the cell.

17. A method for reducing the proliferation of a tumor cell in a mammal, the method comprising administering under suitable conditions an effective amount of an adenoviral expression vector comprising: a) a partial or total deletion of a protein IX-encoding DNA sequence, and b) a gene encoding a suicide protein or a biologically active fragment thereof; and a therapeutic agent that in the presence of the suicide protein is toxic to the tumor cell.

18. The method of claim 17, wherein the therapeutic agent is a thymidine kinase metabolite or a functional equivalent thereof.

19. The method of claim 17, wherein the thymidine kinase metabolite is ganciclovir or 6-methoxypurine arabinonucleoside or a functional equivalent thereof.

20. The method of claim 17, wherein the adenoviral expression vector is administered by injection into the tumor mass.

21. The method of claim 17, wherein the tumor cell is hepatocellular carcinoma.

22. The method of claim 17, wherein the adenoviral expression vector is administered directly into the hepatic artery of the subject.

23. The method of claim 17, wherein the suicide protein is a functional thymidine kinase protein, a functional *E. coli* DEO Δ protein, or a functional cytosine deaminase protein.

24. The method of claim 17, wherein the recombinant adenovirus expression vector further comprises a deletion of a non-essential DNA sequence in adenovirus early region 3 or early region 4.

25. The method of claim 17, wherein the recombinant adenovirus expression vector further comprises a deletion of DNA sequences designated adenovirus E1a and E1b.

26. The method of claim 17, wherein the recombinant adenovirus expression vector further comprises a deletion of early region 3 or 4 and DNA sequences designated adenovirus E1a and E1b.

27. The method of claim 17, wherein the recombinant adenovirus expression vector is a Group C adenovirus selected from a serotype 1, 2, 5 or 6.

28. The method of claim 17, wherein the recombinant adenovirus expression vector is selected from the group consisting of A/C/N/53 or A/M/N/53.

29. The method claim 17, further comprising administering a therapeutic agent that controls cell cycle progression and/or induces cell death.

30. The method of claim 17, wherein the tumor cell is a human tumor cell.

31. A kit for reducing the proliferation of tumor cells comprising the components of the adenoviral expression vector of claim 17, a thymidine kinase metabolite or functional equivalent thereof, pharmaceutical carriers and instructions for the treatment of hepatocellular carcinoma using the kit components.

32. The method of claim 26, wherein the recombinant adenovirus expression vector further comprises a deletion of up to forty nucleotides positioned 3' to the site of the adenovirus E1a and E1b DNA sequence deletions, and the site of the partial or total deletion of the protein IX-encoding sequence, and wherein said foreign functional protein comprises a polyadenlyation signal.

* * * * *